United States Patent
Evans

(10) Patent No.: US 11,439,646 B2
(45) Date of Patent: Sep. 13, 2022

(54) ANTI-PROLIFERATIVE AGENTS FOR TREATING PAH

(71) Applicant: Pfizer Inc., New York, NY (US)

(72) Inventor: Steven Martin Evans, Bedford, MA (US)

(73) Assignee: Pfizer Inc., New York, NY (US)

( * ) Notice: Subject to any disclaimer, the term of this patent is extended or adjusted under 35 U.S.C. 154(b) by 1 day.

(21) Appl. No.: 17/089,154

(22) Filed: Nov. 4, 2020

(65) Prior Publication Data

US 2021/0186974 A1 Jun. 24, 2021

Related U.S. Application Data

(63) Continuation of application No. 16/343,566, filed as application No. PCT/IB2017/056226 on Oct. 9, 2017, now Pat. No. 10,849,903.

(60) Provisional application No. 62/548,629, filed on Aug. 22, 2017, provisional application No. 62/410,566, filed on Oct. 20, 2016.

(51) Int. Cl.
| | | |
|---|---|---|
| *A61K 31/519* | (2006.01) | |
| *A61K 45/06* | (2006.01) | |
| *A61P 9/12* | (2006.01) | |
| *A61P 11/00* | (2006.01) | |
| *A61K 31/5575* | (2006.01) | |

(52) U.S. Cl.
CPC ............ *A61K 31/519* (2013.01); *A61K 45/06* (2013.01); *A61P 9/12* (2018.01); *A61P 11/00* (2018.01); *A61K 31/5575* (2013.01)

(58) Field of Classification Search
CPC .. A61K 31/519; A61K 45/06; A61K 31/5575; A61P 11/00
See application file for complete search history.

(56) References Cited

U.S. PATENT DOCUMENTS

2007/0179118 A1 8/2007 Barvian et al.

FOREIGN PATENT DOCUMENTS

| | | |
|---|---|---|
| CN | 104758292 | 7/2015 |
| EP | 1097711 | 5/2001 |
| WO | 2009/047359 | 4/2009 |
| WO | 2014/128588 | 8/2014 |
| WO | 2015/155197 | 10/2015 |

OTHER PUBLICATIONS

Roskoski, Robert, et al., "Cyclin-dependent protein kinase inhibitors including palbociclib as anticancer drugs", Pharmacological Research, vol. 107, pp. 249-275 (2016).

Schermuly, R.T., et al., "Mechanisms of disease: Pulmonary arterial hypertension", Nature Reviews Cardiology, vol. 8(8), pp. 443-455 (2011).

Galie, N., et al., "The new clinical trials on pharmacological treatment in pulmonary arterial hypertension", European Respiratory Journal, vol. 20(4), pp. 1037-1049 (2002).

(Continued)

*Primary Examiner* — San Ming R Hui
(74) *Attorney, Agent, or Firm* — Richard V. Zanzalari

(57) ABSTRACT

Pulmonary hypertension and related diseases, like pulmonary arterial hypertension, can be treated by administering an effective dose of a CDK inhibitor, including palbociclib, 6-acetyl-8-cyclopentyl-5-methyl-2-{[5-(piperazin-1-yl)pyridin-2yl]amino}pyrido[2,3-d]pyrimidin-7(8H)-one, or pharmaceutically acceptable salt thereof.

3 Claims, 17 Drawing Sheets

(56) References Cited

OTHER PUBLICATIONS

Figure 1A:
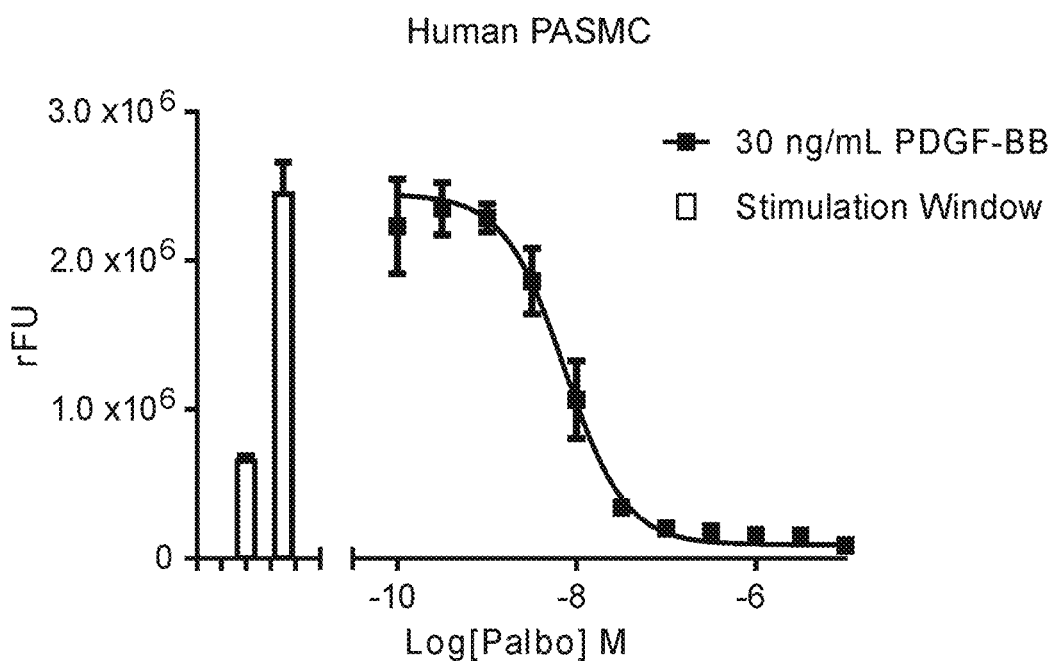

Chattergoon et al., "Antiproliferative effects of calcitonin gene-related peptide in aortic and pulmonary artery smooth muscle cells." Am. J. Physiol. Lung Cell Mol. Physiol. Jan. 2005; 288(1):L202-211.

Guignabert, Christophe, et al., "Pathogenesis of pulmonary arterial hypertension: lessons from cancer", European Respiratory Review, 2013, pp. 543-551, vol. 22.

Happe, C.M. et al., "Peconciling paradigms of abnormal pulmonary blood flow and quasi-malignant cellular alterations in pulmonary arterial hypertension", Vascular Pharmacology, 2016, pp. 17-25, vol. 83.

Lazuktina, V.K., et al., "Pulmonary capillary hemangiomatosis is one of causes of pulmonary arterial hypertension. (literature review)", Medical visualization, OOO "Vidar", M., 2009, 1, pp. 76-82. English Translation.

Mei, Xiao-Long, et al., "Sildenafil inhibits the growth of human colorectal cancer in vitro and in vivo", American Journal of Cancer Research, 2015, pp. 3311-3324, 5(11).

Russian Application No. 2019111887, Office Action, dated Jun. 22, 2020, 3 pages.

Taiwan Patent Application No. 106135422—Office Action and Search Report, dated Aug. 9, 2018, 3 pages.

Volkov, A.V., et al., "Effect of sildenafil on clinical evidence and hemodynamic parameters in patients with pulmonary arterial hypertension, associated with systemic rheumatic diseases". Sistemnye gipertenzii, 2014, 3, pp. 61-66. English Translation.

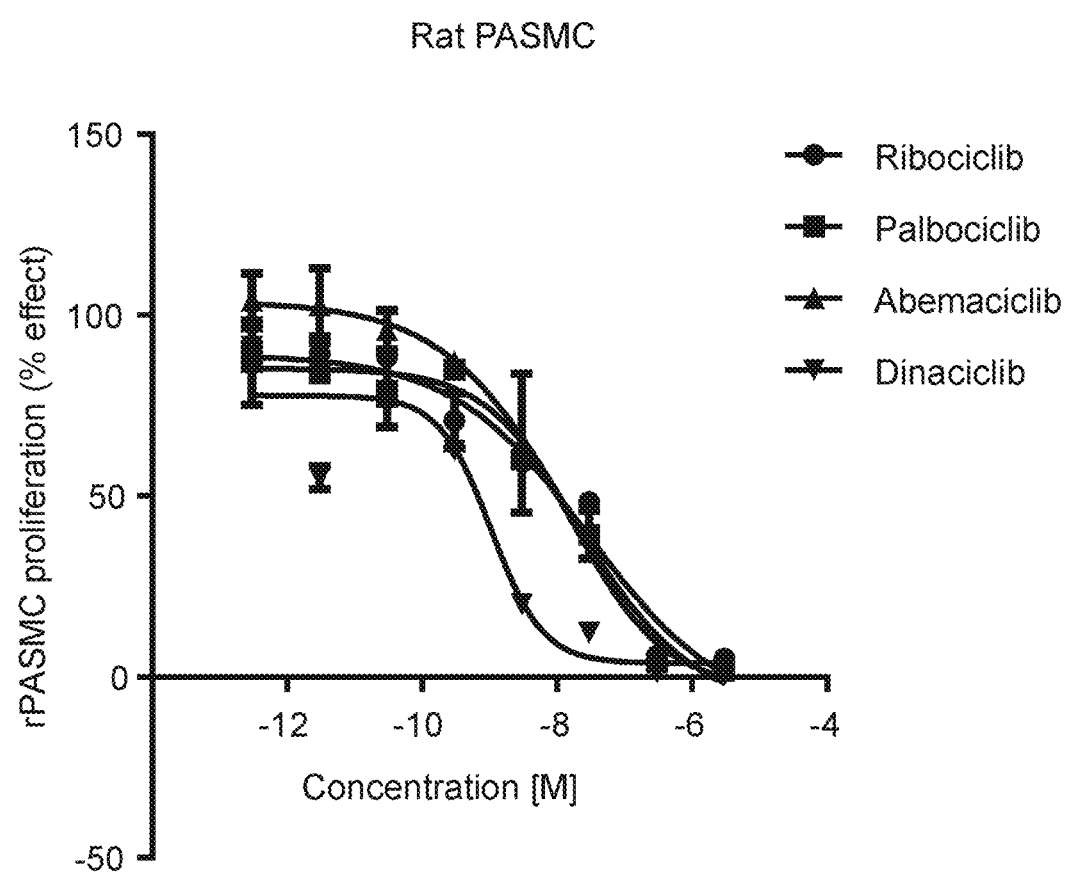

ANTI-PROLIFERATIVE AGENTS FOR TREATING PAH

This application is a continuation of U.S. patent application Ser. No. 16/343,566 filed Apr. 19, 2019, which in turn is a national phase filing under 35 U.S.C. § 371 of international patent application number PCT/IB2017/056226 filed Oct. 9, 2017, which in turn claims the benefit of priority to U.S. Provisional Patent Application Ser. No. 62/410,566 filed Oct. 20, 2016 and to U.S. Provisional Patent Application Ser. No. 62/548,629 filed Aug. 22, 2017, the disclosure of each of these applications is hereby incorporated by reference in its entirety.

FIELD OF INVENTION

Pulmonary hypertension and related diseases, like pulmonary arterial hypertension, can be treated by administering an effective dose of a CDK inhibitor, including palbociclib, 6-acetyl-8-cyclopentyl-5-methyl-2-{[5-(piperazin-1-yl)pyridin-2yl]amino}pyrido[2,3-d]pyrimidin-7(8H)-one.

BACKGROUND OF THE INVENTION

Pulmonary hypertension (PH) has been previously classified as primary (idiopathic) or secondary. Recently, the World Health Organization (WHO) has classified pulmonary hypertension into five groups: Group 1: pulmonary arterial hypertension (PAH); Group 2: PH with left heart disease; Group 3: PH with lung disease and/or hypoxemia; Group 4: PH due to chronic thrombotic and/or embolic disease; and Group 5: miscellaneous conditions (e.g., sarcoidosis, histiocytosis X, lymphangiomatosis and compression of pulmonary vessels).

Pulmonary arterial hypertension (PAH) is a serious, complex, progressive and life-threatening disease of the pulmonary vasculature, characterized by profound vasoconstriction and an abnormal proliferation of smooth muscle cells in the walls of the pulmonary arteries. Severe narrowing of the blood vessels in the lungs leads to very high pulmonary arterial pressures. These high pressures make it difficult for the heart to pump blood through the lungs to be oxygenated. Patients with PAH suffer from extreme shortness of breath as the heart struggles to pump against these high pressures. Patients with PAH typically develop significant increases in pulmonary vascular resistance (PVR) and sustained elevations in pulmonary artery pressure (PAP), which ultimately lead to right ventricular failure and death. Patients diagnosed with PAH have a poor prognosis and equally compromised quality of life, with a mean life expectancy of 2 to 5 years from the time of diagnosis if untreated.

Current methods of treating PAH focus on reducing symptoms and prolonging patient lifespan and enhancing quality of life. Such therapeutic methods include administration of: vasodilators such as prostacyclin, epoprostenol, and sildenafil; endothelin receptor antagonists such as bosentan; calcium channel blockers such as amlodipine, diltiazem, and nifedipine; anticoagulants such as warfarin; supplemental oxygen therapy and diuretics. When medical treatment fails, the final therapeutic option is lung and/or heart-lung transplantation. Each of these methods, however, suffers from one or multiple drawbacks such as lack of effectiveness, serious side effects, low patient compliance, and the inability to prevent PAH. Accordingly, better methods for treating PAH are needed. The present invention addresses these needs.

SUMMARY OF THE INVENTION

The present invention provides a method of treating PAH and other related diseases and conditions by administering a therapeutically effective dose of a CDK inhibitor, including palbociclib.

Two key cell types involved in progression towards PAH are Pulmonary Arterial Smooth Muscle Cells (PASMCs) and Pulmonary Artery Adventitial Fibroblasts (PAAFs). The present invention is based, in part, on the discovery that palbociclib significantly affected the anti-proliferative effects in human and rat PASMCs and human PAAFs. Palbociclib also significantly affected changes in hemodynamics, pulmonary vascular cell proliferation, pulmonary artery morphology, and right ventricle hypertrophy in PAH models.

Palbociclib is a potent and selective inhibitor of CDK4 and CDK6, having the structure:

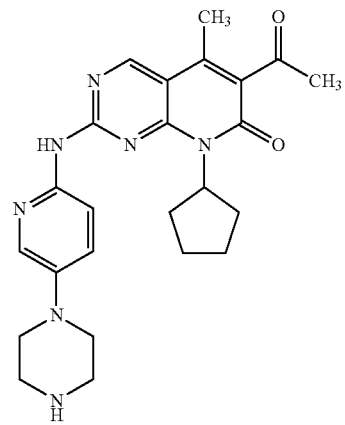 [SMILES: CC(=O)c1c(C)c2cnc(Nc3ccc(N4CCNCC4)cn3)nc2n(C2CCCC2)c1=O]

Palbociclib is described in *WHO Drug Information*, Vol. 27, No. 2, page 172 (2013). Palbociclib and pharmaceutically acceptable salts and formulations thereof are disclosed in International Publication No. WO 2003/062236 and U.S. Pat. Nos. 6,936,612, 7,208,489 and 7,456,168; International Publication No. WO 2005/005426 and U.S. Pat. Nos. 7,345,171 and 7,863,278; International Publication No. WO 2008/032157 and U.S. Pat. No. 7,781,583; International Publication No. WO 2014/128588; and International Application No. PCT/IB2016/053040. The contents of each of the foregoing references are incorporated herein by reference in their entirety.

Palbociclib is approved in the United States for the treatment of hormone receptor (HR)-positive, human epidermal growth factor 2 (HER2)-negative advanced or metastatic breast cancer in combination with letrozole as initial endocrine therapy in postmenopausal women or in combination with fulvestrant following disease progression on endocrine therapy.

In another embodiment of the invention, palbociclib is administered to a subject diagnosed with or at risk of developing pulmonary hypertension or PAH including, but are not limited to, idiopathic PAH, hereditary or familial PAH, and secondary pulmonary hypertension (e.g. hypertension resulting from pulmonary emboli, emphysema, pulmonary fibrosis, and congenital heart disease). In one embodiment, the subject is diagnosed with idiopathic PAH or hereditary PAH. In some embodiments, the subject at risk of developing PAH has a mutation in the gene encoding the bone morphogenetic protein type-2 receptor.

The present invention also includes a kit for the treatment or prevention of pulmonary arterial hypertension. In one embodiment, the kit comprises palbociclib and an administration device. The administration device can be designed for pulmonary delivery, such as inhalers, nebulizers, insufflators, droppers, and aerosolizers. In other embodiments, the administration device can be designed for intravenous or intra-arterial delivery, such as a catheter. Palbociclib may be optionally formulated to be stored in the administration device. The kit may further comprise instructions for administering palbociclib to a subject (e.g, human) for treating or preventing PAH or other diseases discussed herein. In one embodiment, the instructions elaborate and qualify the mode of administration, for example, by specifying the days of administration for palbociclib during a 28 day cycle.

BRIEF DESCRIPTION OF THE DRAWING(S)

Figure 1B:
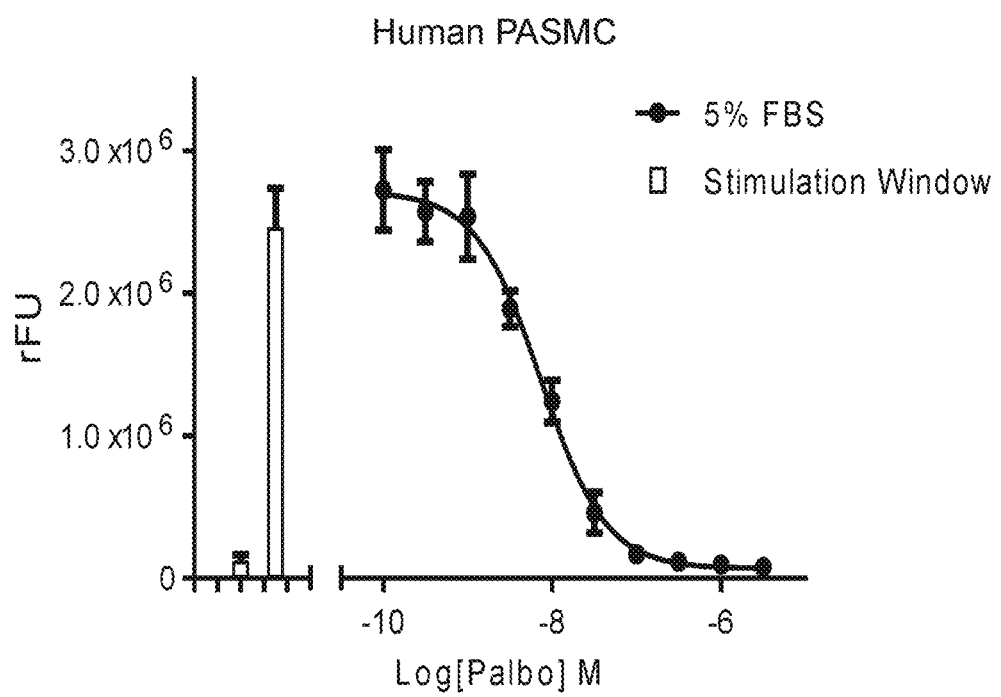
Figure 1C:
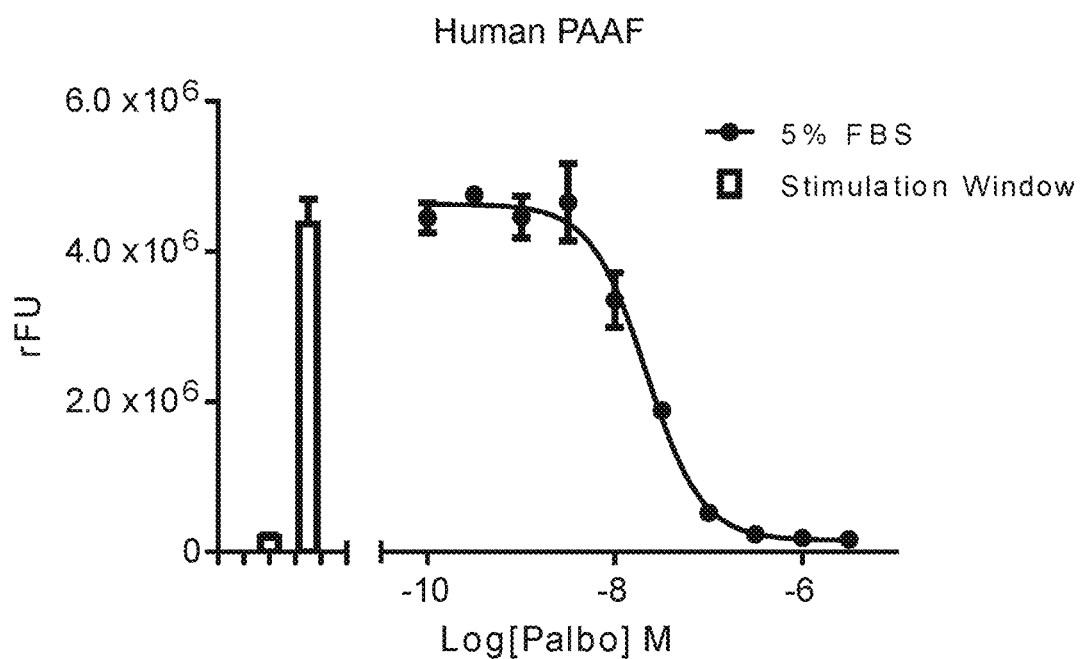
Figure 1D:
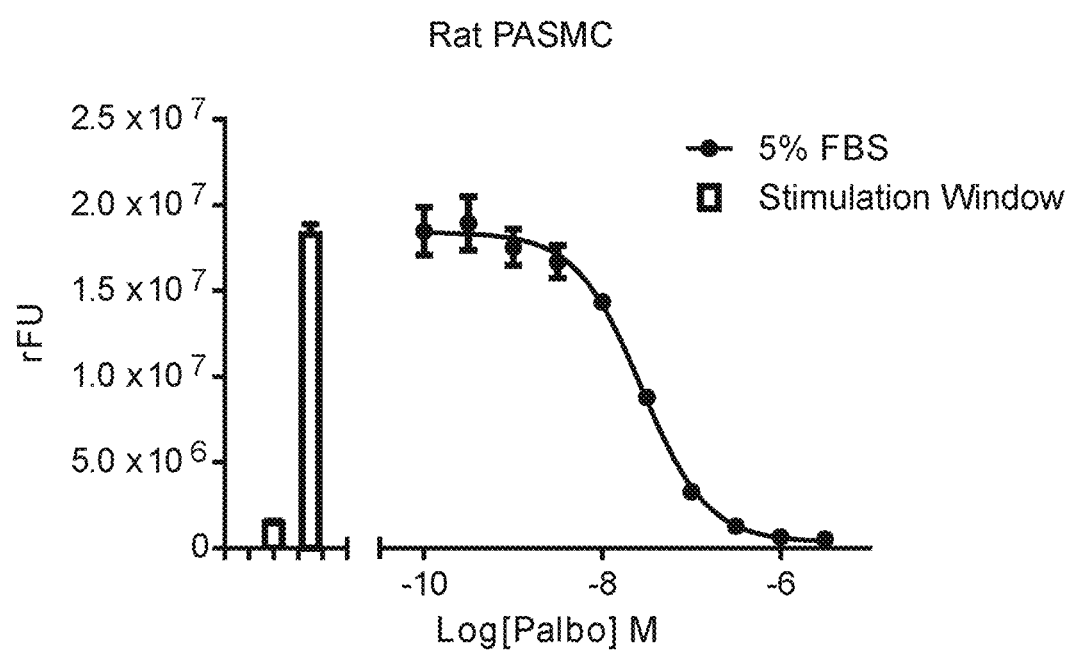

FIG. 1a to FIG. 1g. Cell Proliferation: BrdU incorporation assays were conducted to measure cellular DNA synthesis rates and proliferation, after cells were treated with serially diluted palbociclib. The dose-response curves show that palbociclib potently repressed proliferation of human PASMCs (FIGS. 1a and 1b), human PAAF (FIG. 1c), rat PASMCs (FIG. 1d). EdU incorporation assays were conducted to measure cellular DNA synthesis rates and proliferation, after cells were treated with either serially diluted palbociclib or another known CDK inhibitor. The dose-response curves show repressed proliferation of human PASMCs (FIG. 1e), human PAAF (FIG. 1f), and rat PASMCs (FIG. 1g).

Figure 2A:
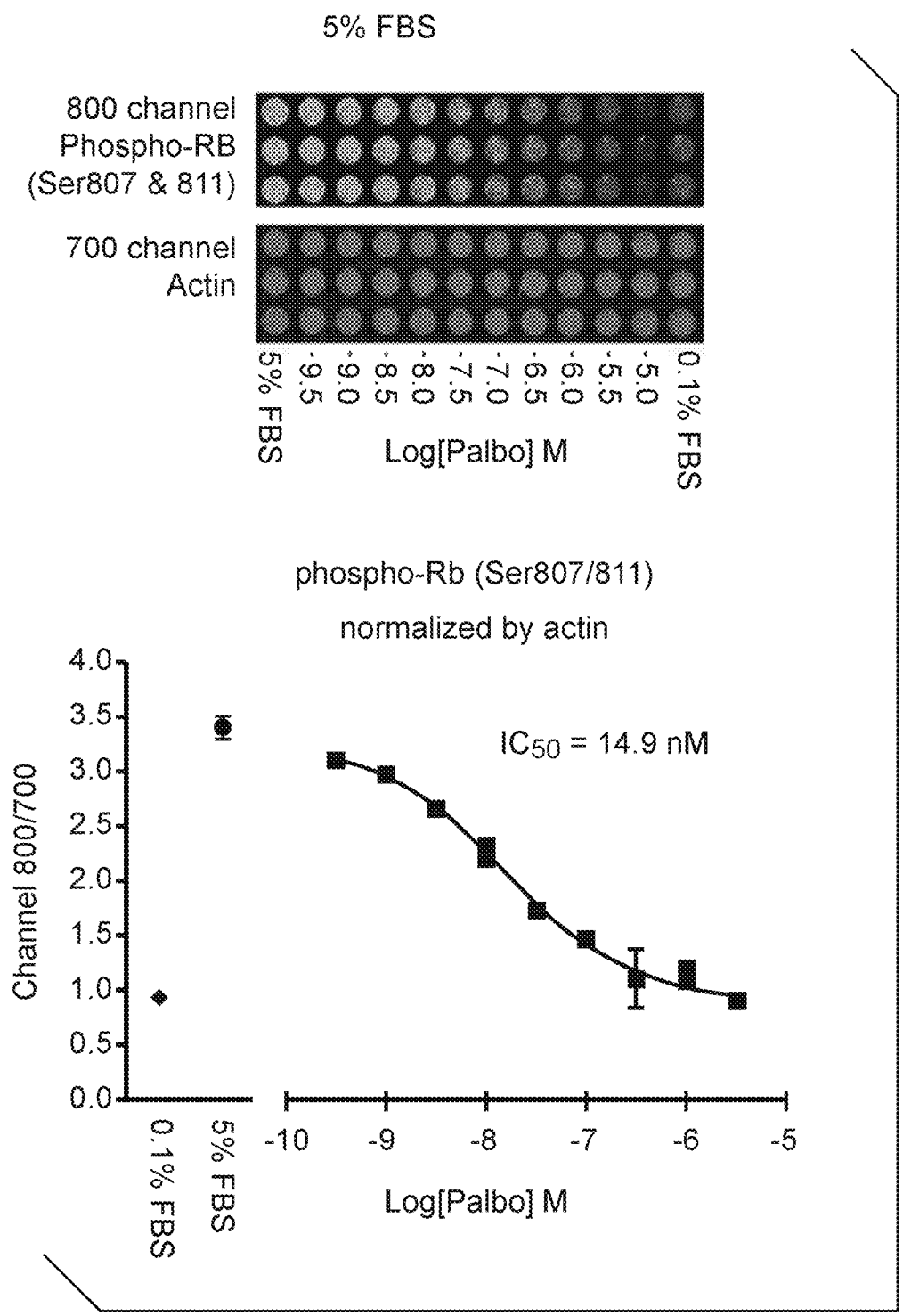
Figure 2B:
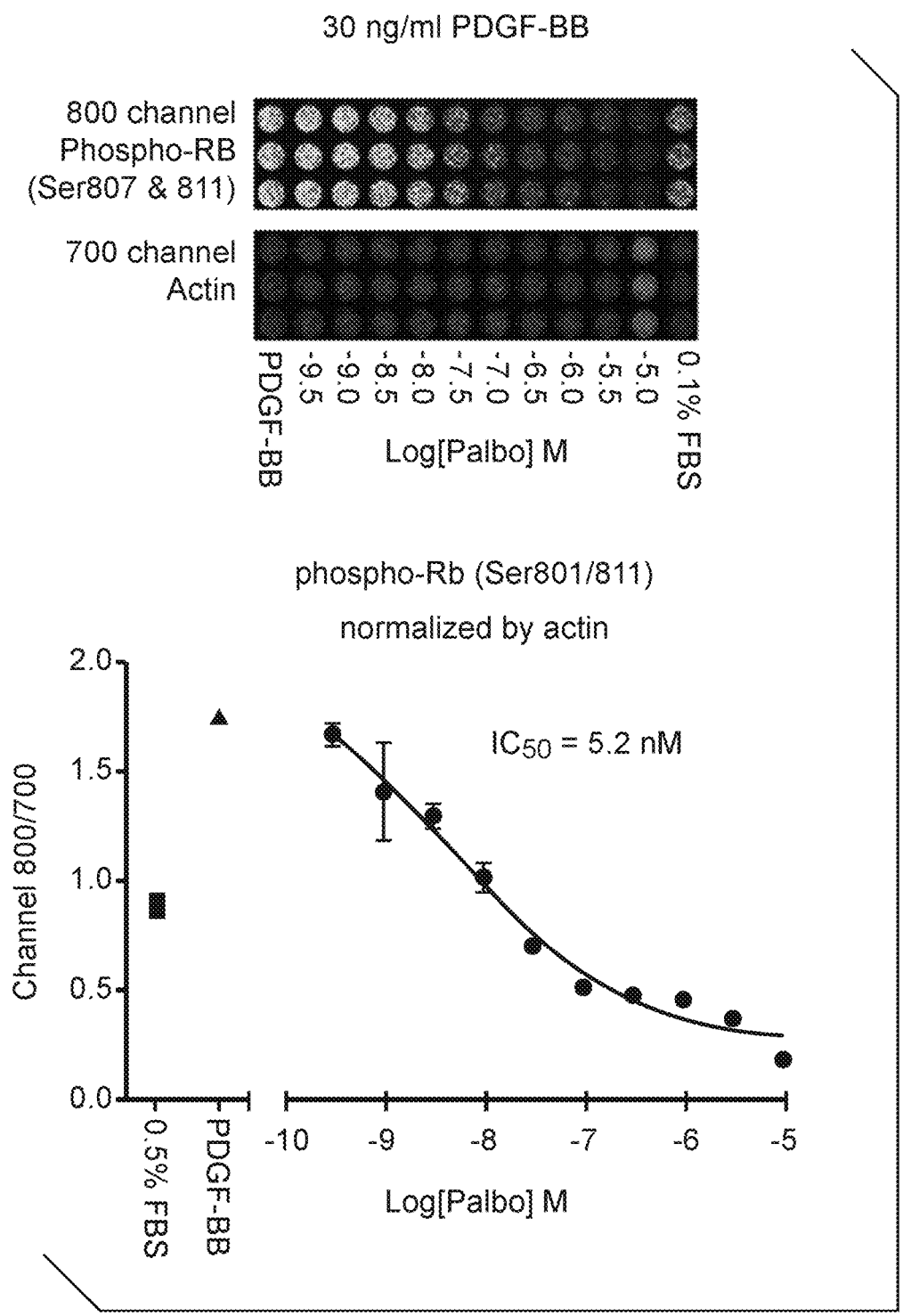
Figure 2C:
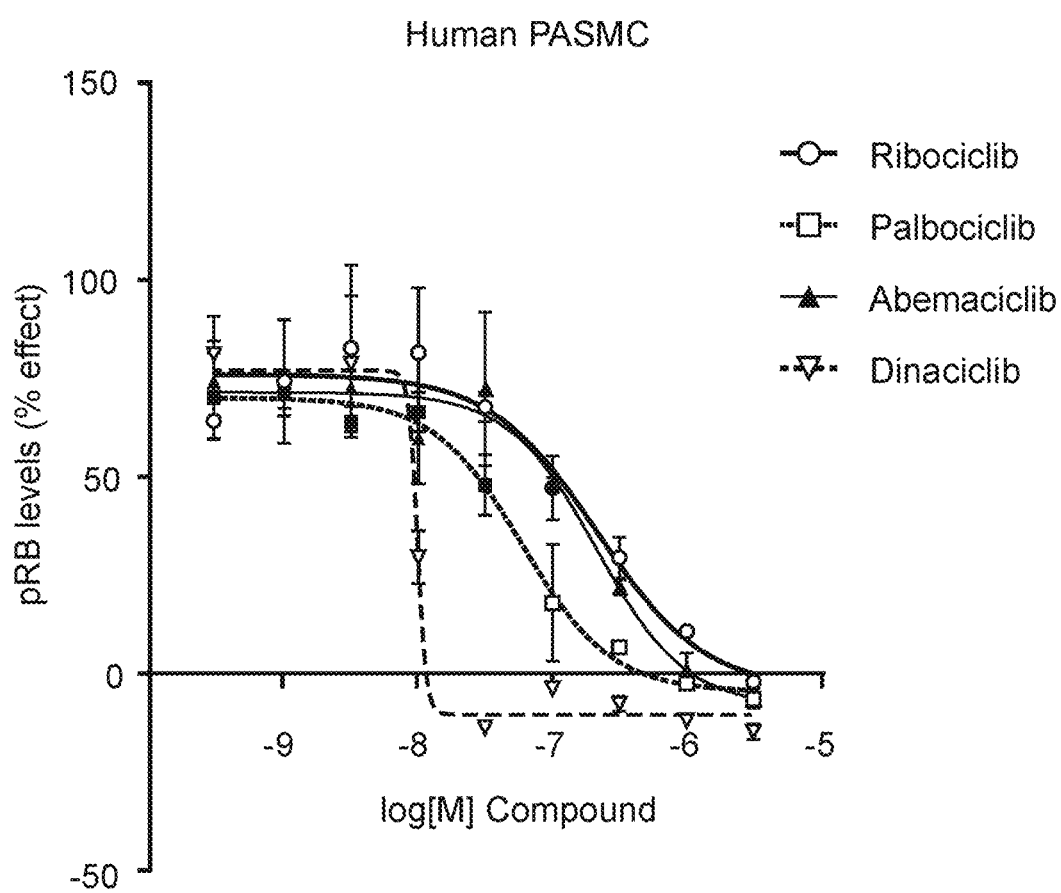

FIG. 2a to FIG. 2c. Rb Phosphorylation: Effects of palbociclib on phosphorylation of retinoblastoma gene product. Palbocliclib potently blocked phoshorylation of Rb (phospho-Rb) at serine 807 and 811 induced by 5% FBS (FIG. 2a) or by PDGF-BB (FIG. 2b) in human primary PASMCs, while it had little effect on total Rb levels. Inhibition of phospho-RB in human primary PASMCs for known CDK inhibitors induced by 10% FBS (FIG. 2c).

Figure 3A:
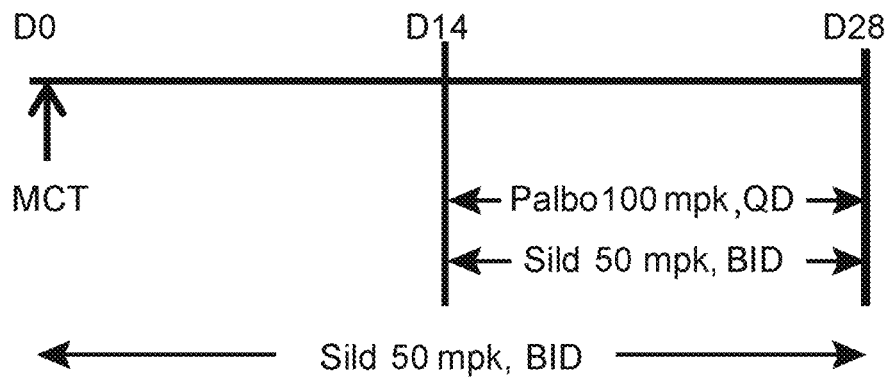
Figure 3B:
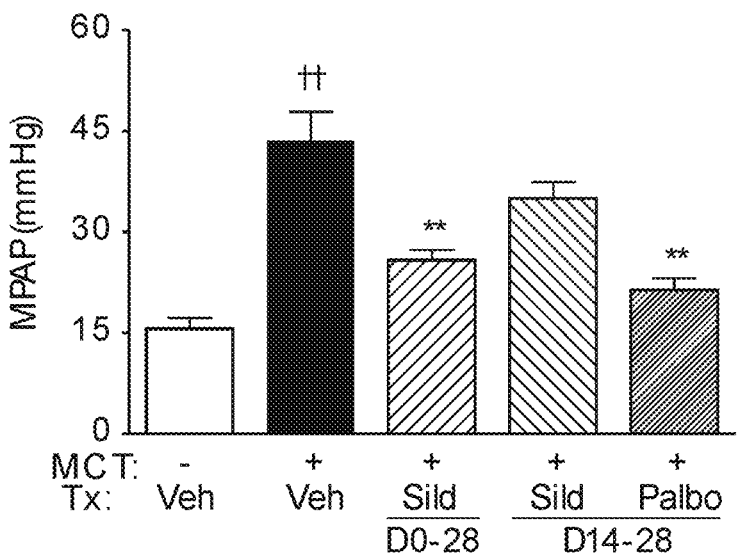
Figure 3C:
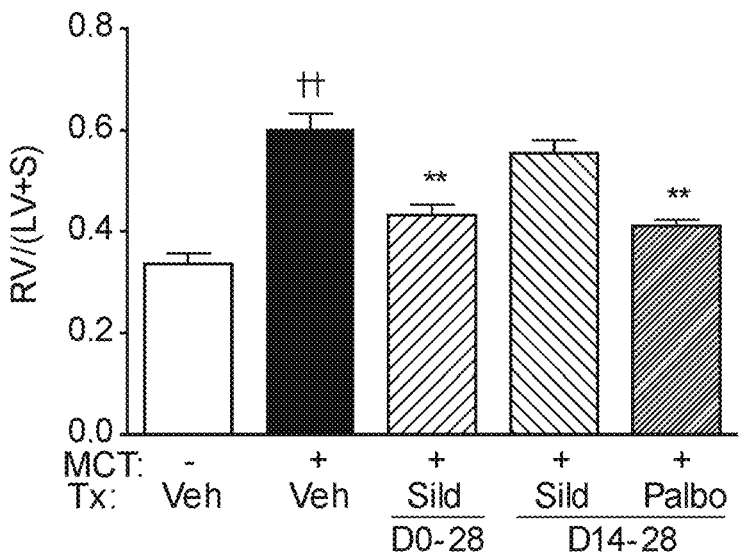
Figure 3D:
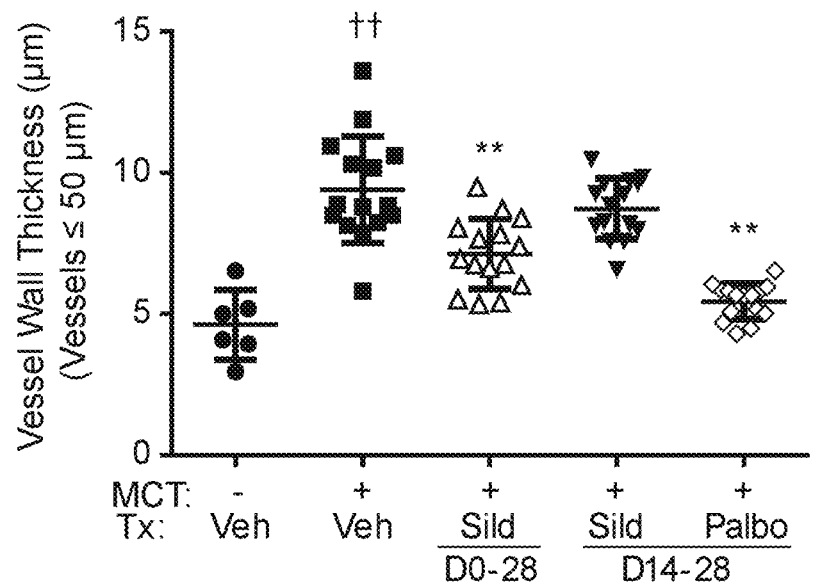
Figure 3E:
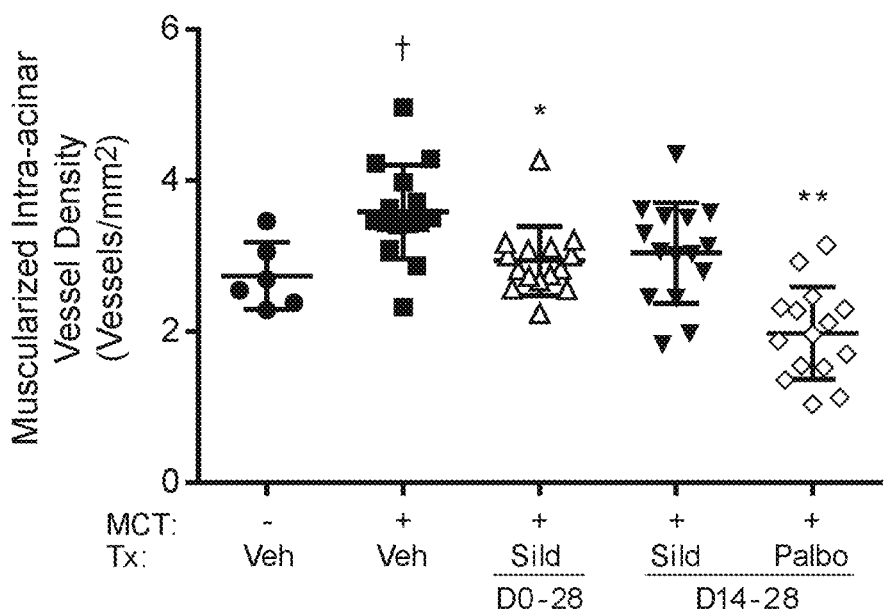
Figure 3F:
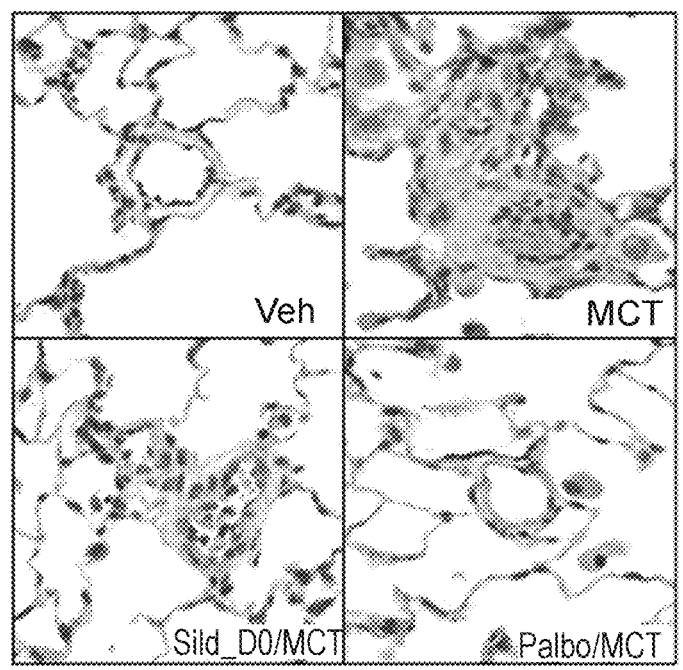
Figure 3G:
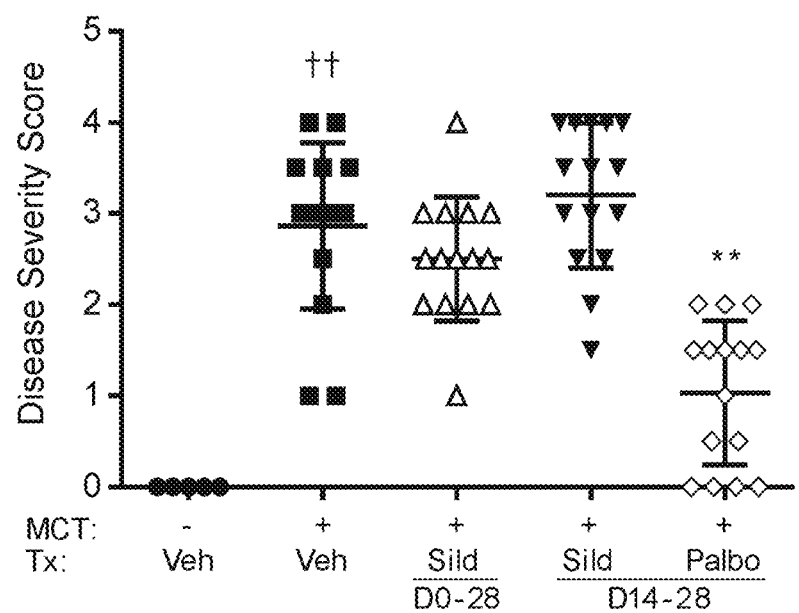
Figure 3H:
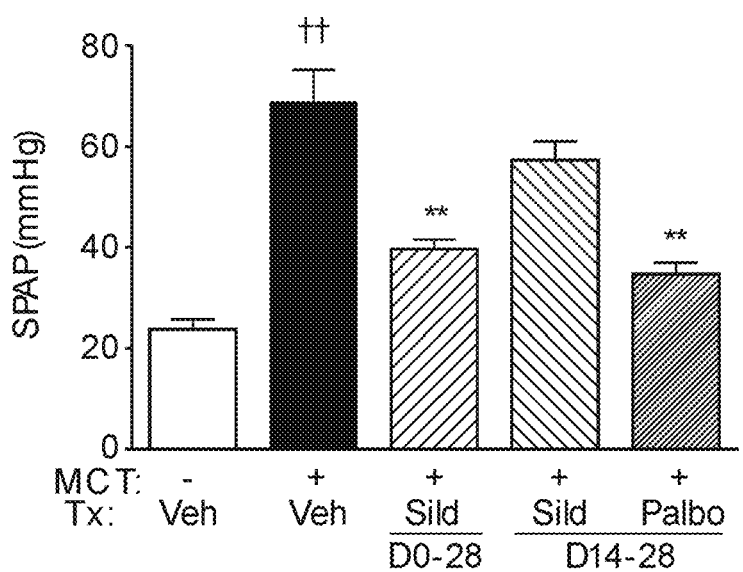
Figure 3I:
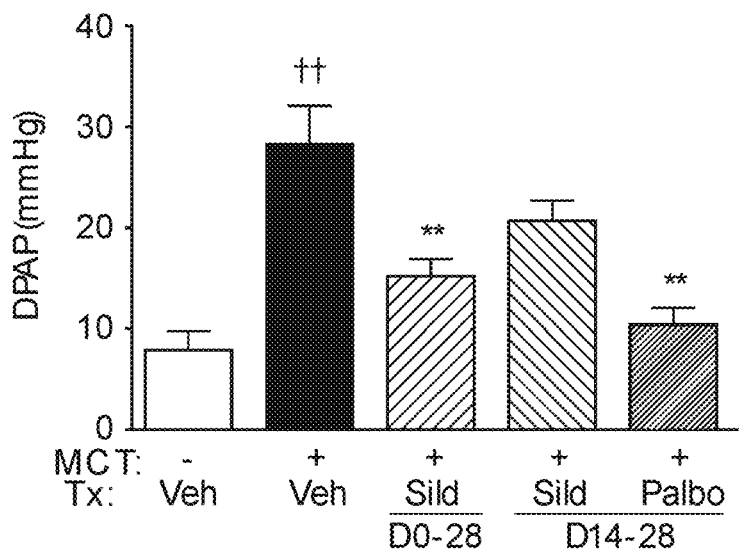
Figure 3J:
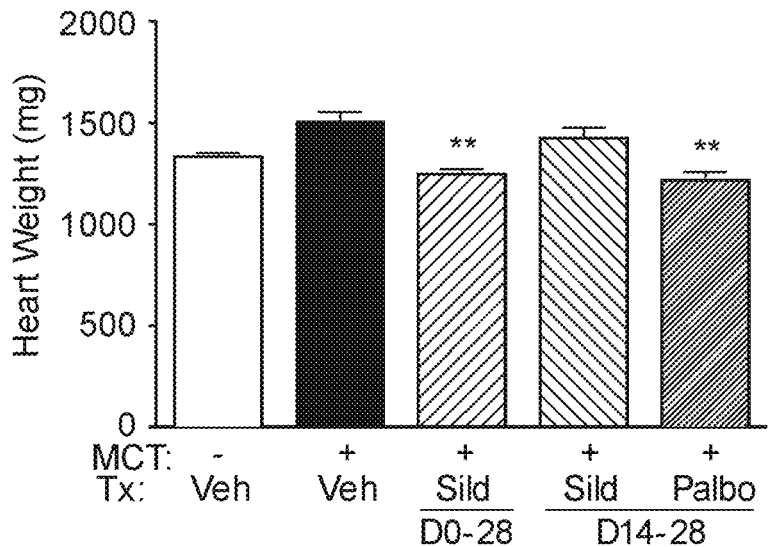

FIG. 3a to FIG. 3j. Hemodynamic and structural changes associated with PAH pathology in the rat monocrotaline (MCT) model. FIG. 3a shows frequency of administration of drugs studied. Experimental results shown as mean pulmonary arterial pressure (MPAP; FIG. 3b), systolic pulmonary arterial pressure (SPAP; FIG. 3h), and diastolic pulmonary arterial pressure (DPAP; FIG. 3i), Fulton's index (RV/(LV+FS); FIG. 3c), Vessel Wall thickness (FIG. 3d), Muscularized intra-acinar vessel density (FIG. 3e), histopathology (FIG. 3f), disease severity scores (FIG. 3g), and heart weight (FIG. 3j).

Figure 4A:
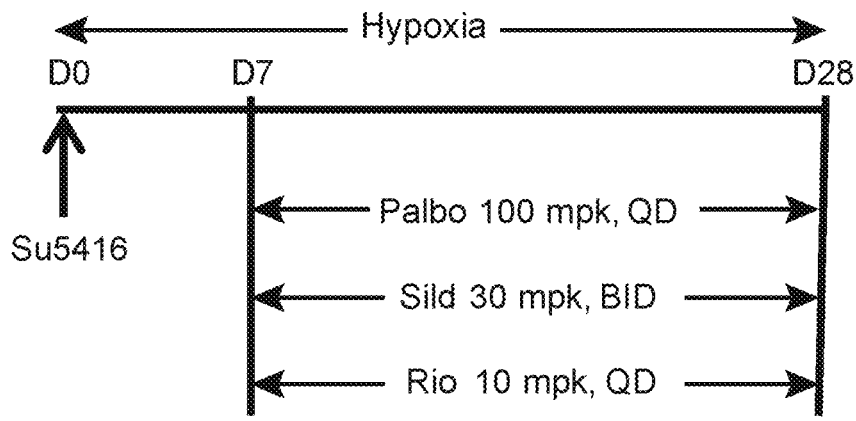
Figure 4B:
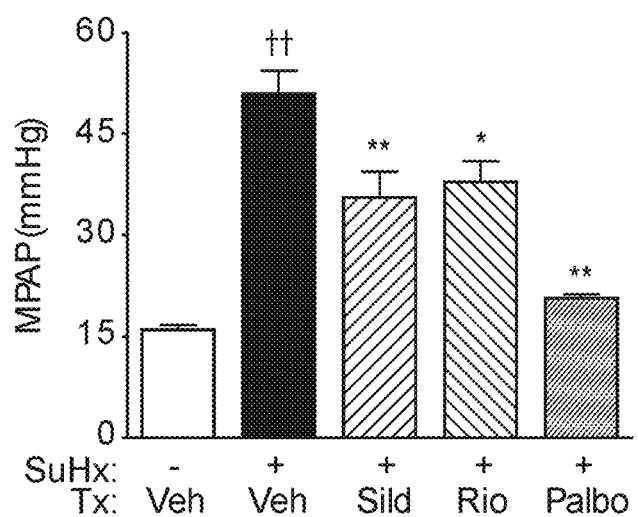
Figure 4C:
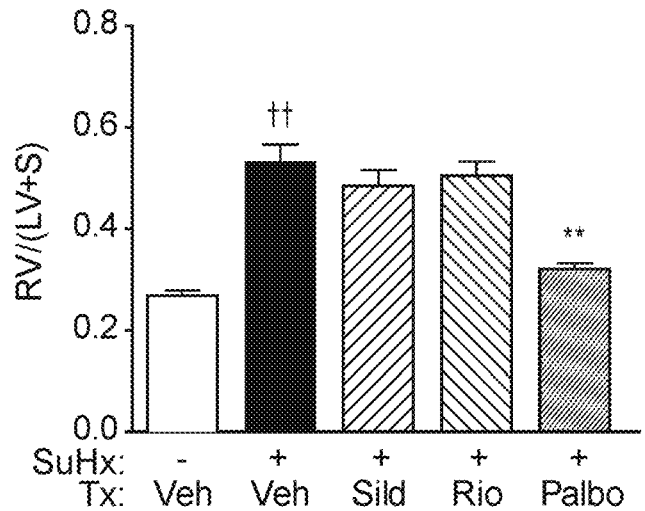
Figure 4D:
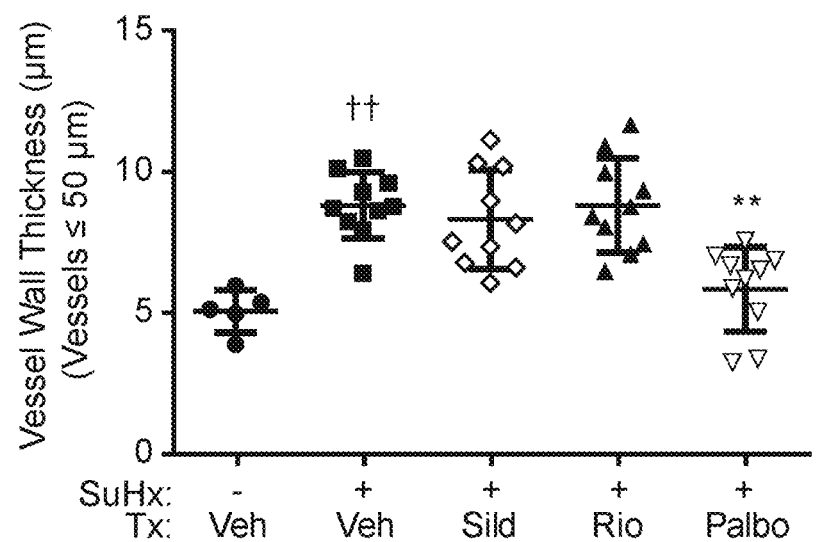
Figure 4E:
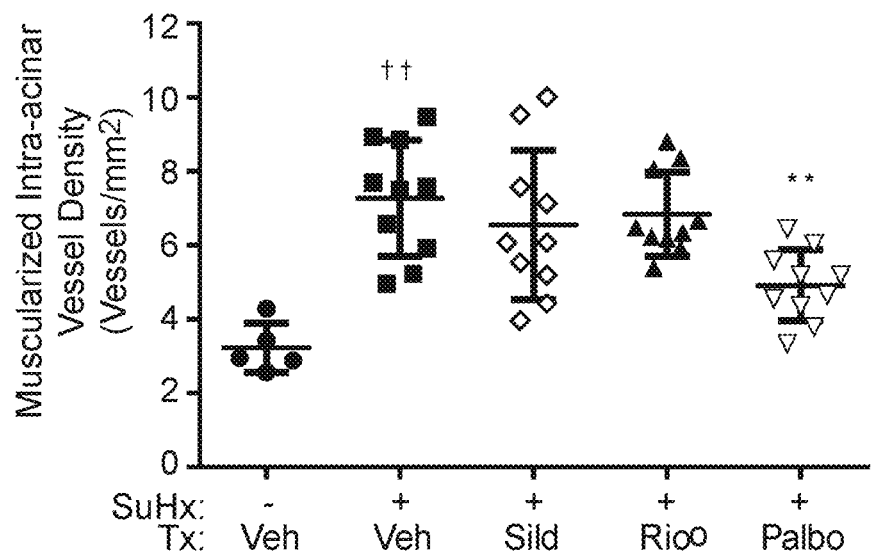
Figure 4F:
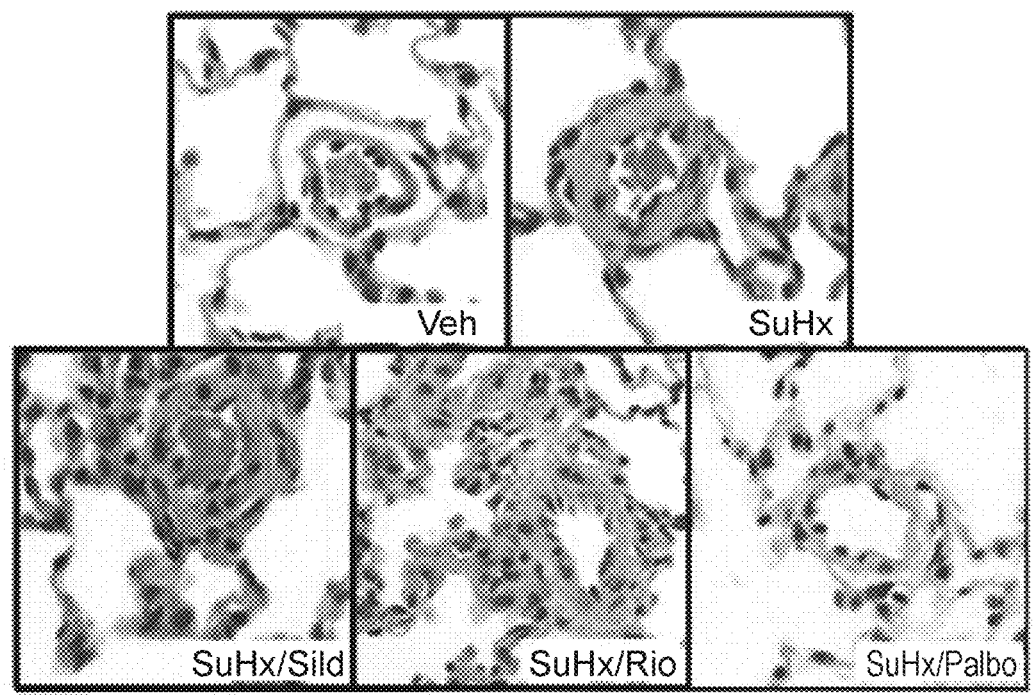
Figure 4G:
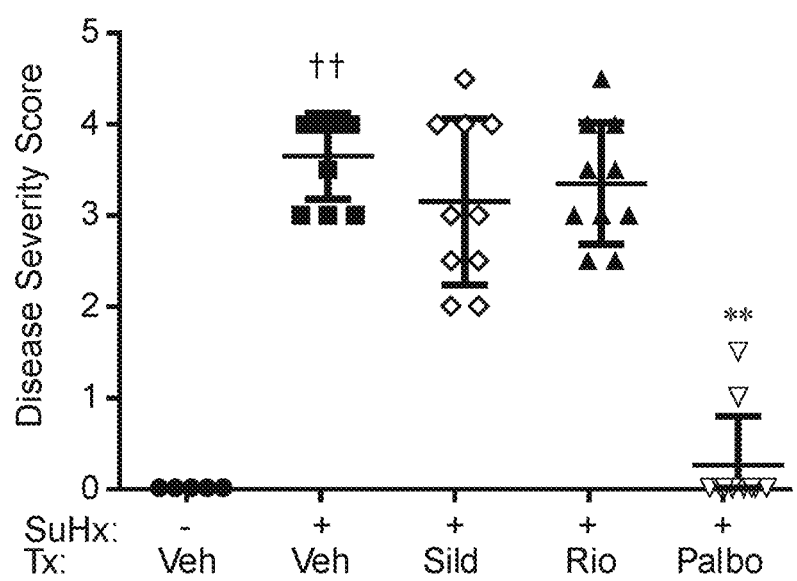
Figure 4H:
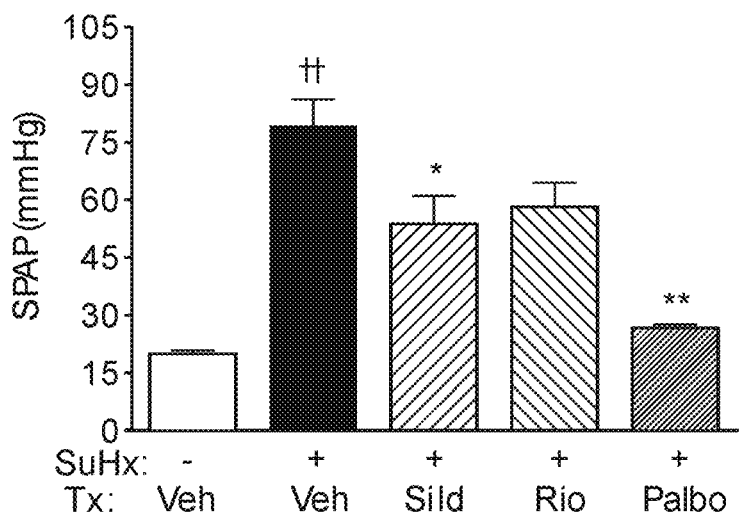
Figure 4I:
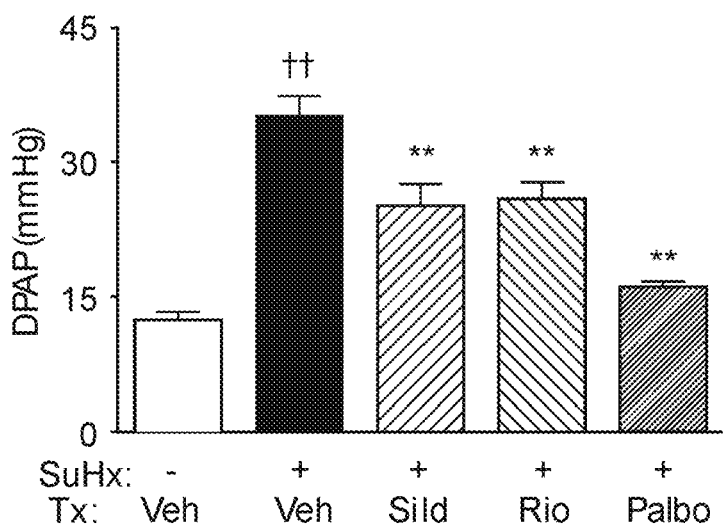
Figure 4J:
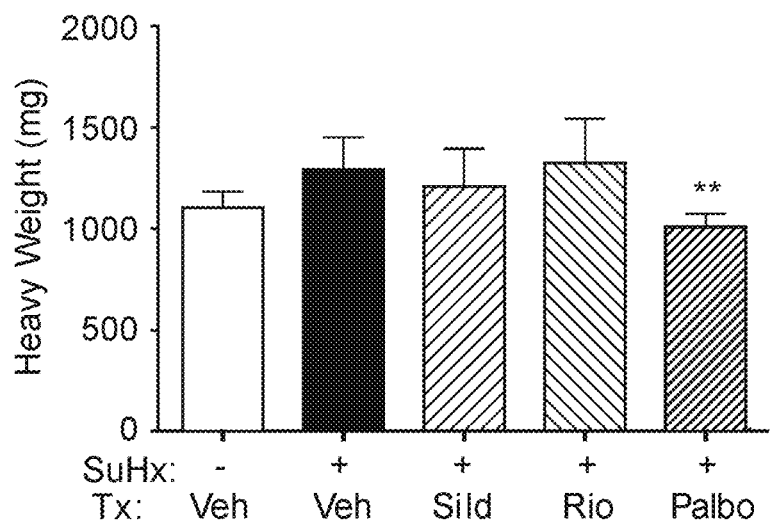

FIG. 4a to FIG. 4j. Hemodynamic changes and significant structural improvement in the pulmonary vasculature in the rat SuHx PAH model. FIG. 4a shows frequency of administration of drugs studied (FIG. 4a). Experimental results shown as mean pulmonary arterial pressure (MPAP; FIG. 4b), SPAP (FIG. 4h), DPAP (FIG. 4i), Fulton's index (RV/(LV+FS), FIG. 4c), Vessel Wall thickness (FIG. 4d), Muscularized intra-acinar vessel density (FIG. 4e), histopathology (FIG. 4f), disease severity scores (FIG. 4g), and heart weight (FIG. 4j).

Figure 5A:
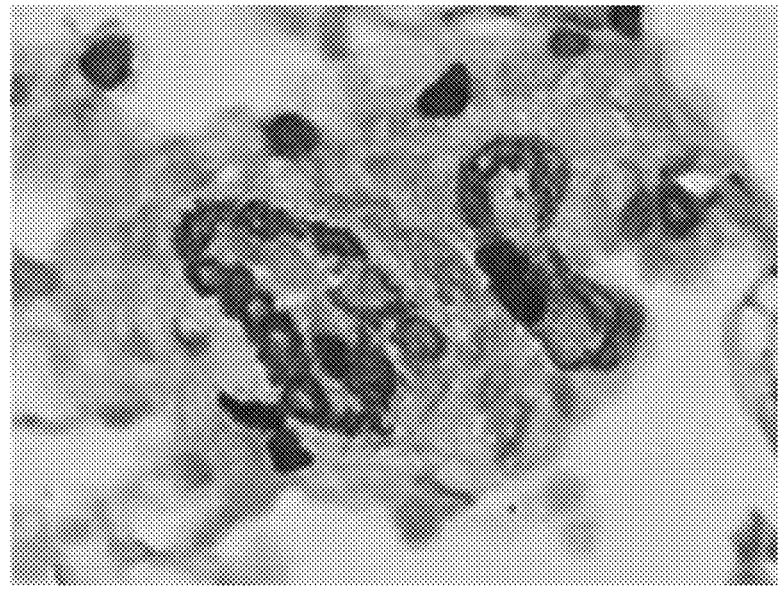
Figure 5B:
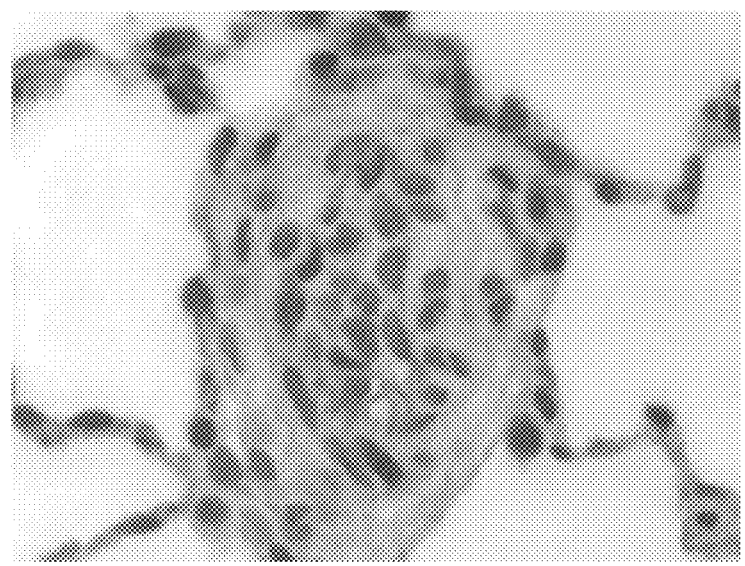
Figure 5C:
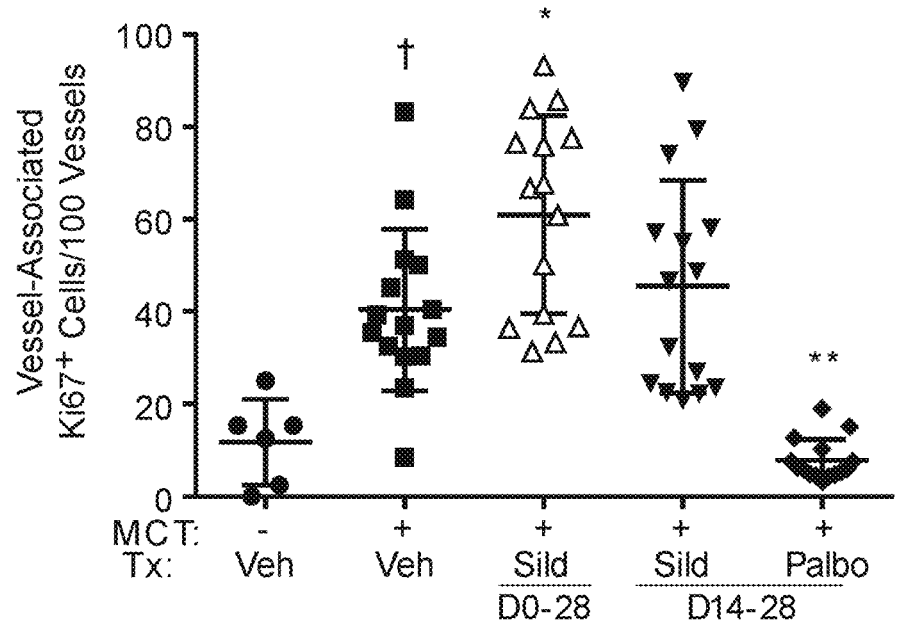
Figure 5D:
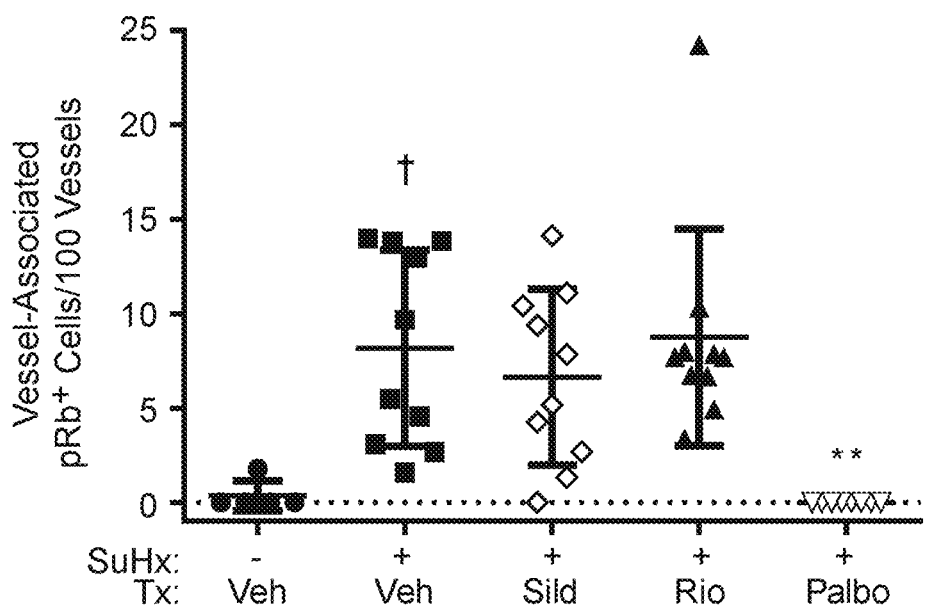

FIG. 5a to FIG. 5d. Cell proliferation evaluated in the pulmonary vasculature. IHC of dual stained αSMA/Ki67 (FIG. 5a) and CD31/phosphoRb (FIG. 5b) in rat lung sections. Experimental results pRb; shown as Ki67 (FIG. 5c) and vessel associated Retinoblastoma protein phosphorylation (FIG. 5d).

DETAILED DESCRIPTION OF THE INVENTION

Pulmonary hypertension, like systemic hypertension, is not a single disease but a group of diseases, which share the defining element of a mean pulmonary arterial pressure ≥25 mm Hg. PH has been classified and divided into 5 groups (Galie et al. ERJ (2009) Dec.; 34(6);1219-63). This invention generally relates to, but is not limited to, treating the World Health Organization (WHO) group 1, or PAH group of, diseases characterized by elevated pulmonary arterial pressure and elevated blood flow resistance due to a pre-capillary pulmonary microangiopathy.

A key feature in the PAH lung is abnormal cellular proliferation, which leads to progressive obliteration of the lumina of the pulmonary vasculature, resulting in pathological increases in vascular resistance. Pulmonary vascular remodeling is an active process of structural change intrinsically linked to modifications in cell growth, cell death, cell migration, cell differentiation, and the synthesis or degradation of extracellular matrix. Schermuly, R. T., et al. Mechanisms of disease: pulmonary arterial hypertension. *Nature reviews. Cardiology* 8, 443-455 (2011). While a number of pharmacological classes already exist as approved therapies in clinical PAH, they primarily induce vasorelaxation and thereby reduce pulmonary vascular resistance. Moreover, monotherapy may be inadequate in light of individual differences of patients. Humbert, M. & Ghofrani, H. A. The molecular targets of approved treatments for pulmonary arterial hypertension. *Thorax* 71, 73-83 (2016). Therefore, these therapies do not address the complexity of vascular remodeling.

Changes in the pulmonary vasculature involve PASMCs, PAAFs, and Pulmonary Arterial Endothelial Cells (PAECs). Guignabert, C, et al. *Pathogenesis of pulmonary arterial hypertension: lessons from cancer. European respiratory review: an official journal of the European Respiratory Society* 22, 543-551 (2013). A recent review of research on PAH discussed proliferation signaling "hubs" to target multiple pathways of signal transduction. Pullamsetti, S S, et al. *American journal of respiratory and critical care medicine* (2016), first published online 14 Sep. 2016 as DOI: 10.1164/rccm.201606-1226PP. Another review contemplated the relationship between changes in pulmonary blood flow the cancer-like changes in endothelial cells of the pulmonary vascular wall. Heppe, C. M., et al. *Vascular Pharmacology* 83 (2016) 17-25.

New approaches have focused on targeting the pro-proliferative phenotype that underpins the pulmonary vascular remodeling in PAH patients, with the aim of achieving improved efficacy and enhanced survival. There have been a few examples in which oncology drugs were shown to be efficacious in slowing down PAH disease progression in preclinical studies. See Savai, R., et al. Pro-proliferative and inflammatory signaling converge on FoxO1 transcription factor in pulmonary hypertension. *Nature medicine* 20, 1289-1300 (2014); Ciuclan, L., et al. Imatinib attenuates hypoxia-induced pulmonary arterial hypertension pathology via reduction in 5-hydroxytryptamine through inhibition of tryptophan hydroxylase 1 expression. *American journal of respiratory and critical care medicine* 187, 78-89 (2013); and Schermuly, R. T., et al. Reversal of experimental pulmonary hypertension by PDGF inhibition. *The Journal of clinical investigation* 115, 2811-2821 (2005).

Cyclin dependent kinases and related serine/threonine protein kinases are important cellular enzymes that perform essential functions in regulating cell division and proliferation. The cyclin dependent kinase catalytic units are activated by regulatory subunits known as cyclins. At least sixteen mammalian cyclins have been identified (Johnson D G, Walker C L. Cyclins and Cell Cycle Checkpoints. Annu. Rev. Pharmacol. Toxicol. (1999) 39:295 312). Cyclin B/CDK1, Cyclin A/CDK2, Cyclin E/CDK2, Cyclin D/CDK4, Cyclin D/CDK6, and likely other heterodynes including CDK3 and CDK7 are important regulators of cell cycle progression. Additional functions of Cyclin/CDK heterodynes include regulation of transcription, DNA repair, differentiation and apoptosis (Morgan DO. Cyclin dependent kinases: engines, clocks, and microprocessors. Annu. Rev. Cell. Dev. Biol. (1997) 13:261 291).

The complexity of pulmonary vascular remodeling provides many pathways for investigation such as targeting cell cycle of proliferation involving proteins known as cyclin-dependent kinases (CDKs). These CDKs associate with specific cyclins to form a holoenzyme complex required for activity. For each step of the proliferative cycle, different cyclins are required, and the relative expression of each cyclin protein increases and/or decreases to periodically activate their specific CDK. Charron, T., et al. The cell cycle: a critical therapeutic target to prevent vascular proliferative disease. *The Canadian journal of cardiology* 22 Suppl B, 41B-55B (2006).

The present invention is based, in part, on the discovery that CDK inhibitors (CDKi's) inhibit the proliferative effects of mitogens in human and rat PASMCs and human PAAFs, and reduce the elevations in hemodynamics, pulmonary vascular cell proliferation, pulmonary artery morphology, and right ventricle hypertrophy in PAH models.

The present invention is further based, in part, on the discovery that palbociclib significantly affected the anti-proliferative effects in human and rat PASMCs and human PAAFs, and significantly affected changes in hemodynamics, pulmonary vascular cell proliferation, pulmonary artery morphology, and right ventricle hypertrophy in PAH models.

Another embodiment of the invention includes a method of treating PAH (pulmonary arterial hypertension) comprising administering to a subject in need thereof an effective amount of 6-acetyl-8-cyclopentyl-5-methyl-2-{[5-(piper-azin-1-yl)pyridin-2yl]amino}pyrido[2,3-d]pyrimidin-7(8H)-one, or pharmaceutically acceptable salt thereof.

Another embodiment of the invention includes a method of treating PAH (pulmonary arterial hypertension) comprising administering to a subject in need thereof an effective amount of 6-acetyl-8-cyclopentyl-5-methyl-2-{[5-(piper-azin-1-yl)pyridin-2yl]amino}pyrido[2,3-d]pyrimidin-7(8H)-one.

Another embodiment of the invention includes a method of treating PAH comprising administering to a subject in need thereof an effective amount of a CDK inhibitor.

Another embodiment of the invention includes a method of treating PAH comprising administering to a subject in need thereof an effective amount of a CDK inhibitor selected from any of the following compounds, or pharmaceutically acceptable salts thereof:

trilaciclib (G1T28), G1T38, alvocidib SEL-24, milciclib, AGM-130, AT 7519, BAY 1143572/1112054, BCD-115, CYC065, FLX 925, SHR 6390, TG-02, A-1467729, ABC 1183, AZD 5576, BPI 1178, senexin, ICEC0942, CCT-68127, CCT-251921, ON 123300, voruciclib, SEL120-34, SRX-3177, TP 1287, SY1365, UD-017, or VS2-370.

Another embodiment of the invention includes a method of treating PAH comprising administering to a subject in need thereof an effective amount of a CDK inhibitor selected from:

1. Ribociclib (7-cyclopentyl-N, N-dimethyl-2-((5-(piper-azin-1-yl)pyridin-2-yl)amino)-7H-pyrrolo[2,3-d]pyrimi-dine-6-carboxamide), or pharmaceutically acceptable salts thereof: A CDKi targeting cyclin D1/CDK4 and cyclin D3/CDK6 cell cycle pathway, with potential antineoplastic activity. Ribociclib specifically inhibits CDK4 and 6;

2. Abemaciclib (2-pyrimidinamine, N-(5-((4-ethyl-1-piperazinyl)methyl)-2-pyridinyl)-5-fluoro-4-(4-fluoro-2-methyl-1-(1-methylethyl)-1H-benzimidazol-6-yl)), or pharmaceutically acceptable salts thereof: A CDKi that targets the CDK4 and CDK6 cell cycle pathway; or 3. Dinaciclib (2-[(2S)-1-[3-ethyl-7-[(1-oxidopyridin-1-ium-3-yl)methylamino]pyrazolo[1,5-a]pyrimidin-5-yl]pip-eridin-2-yl]ethanol), or pharmaceutically acceptable salts thereof: A CDKi that selectively targets CDK1, CDK2, CDKS, and CDK9.

Another embodiment of the invention includes a method of treating PAH comprising administering to a subject in need thereof an effective amount of a CDK inhibitor, or pharmaceutically acceptable salts thereof, as the CDK inhibitor is presented in any one or combination in the non-exclusive list including: WO03/062236, WO07140222, WO10075074, WO10020675, WO16015598, WO16015597, WO16015605, WO16015604, WO2012/066508, WO04004632, WO11026911, WO11026904, WO 2011/101409, WO2006/074985, WO2012/061156, WO1000913, WO10009155, and WO0183469.

Related diseases to be treated include any one or more or combination of the following: pulmonary capillary hemangiomatosis (PCH) (Group 1), pulmonary hypertension due to left heart disease (Group 2 PH), pulmonary hypertension due to lung disease and/or hypoxia (Group 3), chronic thromboembolic pulmonary hypertension (Group 4), pulmonary hypertension with unclear or multifactorial etiologies (Group 5), idiopathic forms of pulmonary vascular disease, or a lung disorder that including any form of acute and chronic lung injury and inflammation (ARDS, ILD, pneumonia, COPD, asthma), or primary lung vascular disorders (idiopathic, collagen vascular-associated, liver disease-associated, drug-associated, HIV-associated, blood clot-induced pulmonary hypertension). Another embodiment of the invention includes a method of treating related diseases discussed herein comprising administering to a subject in need thereof an effective amount of 6-acetyl-8-cyclopentyl-5-methyl-2-{[5-(piperazin-1-yl)pyridin-2yl]amino}pyrido[2,3-d]pyrimidin-7(8H)-one, or pharmaceutically acceptable salt thereof or no such salt.

Palbociclib was examined for its activity in PDGF-BB or serum-induced proliferation of human and rat PASMCs. See Example 1. Palbociclib potently inhibited PDGF-BB induced proliferation of human primary PASMCs with an $IC_{50}$ of 7.4 nM, average of 3 (FIG. 1a) obtained by BrdU, and expressed as relative fluorescence units (rFU). Proliferation of both human and rat primary PASMCs induced by 5% fetal bovine serum (FBS) was similarly inhibited by palbociclib treatment ($IC_{50}$=7.4 nM and 27.4 nM, respectively, each is an average of 3) (FIG. 1b and FIG. 1d). Palbociclib was also very potent against another cell type involved in vascular remodeling, the adventitial fibroblast (PAAF). Serum-induced proliferation of human primary PAAFs was inhibited with an $IC_{50}$ of 21.6 nM, average of 3 (FIG. 1c).

To demonstrate the anti-proliferative effects of CDK inhibitors on PASMCs and PAAF were achieved via the pharmacological inhibition of CDK activity, three additional compounds (abemaciclib, dinaciclib and ribociclib) were profiled in parallel to palbociclib. Table 1 provides the $IC_{50}$ values based on the % effect of proliferation as presented in FIGS. 1e, 1f, and 1g.

Figure 1E:
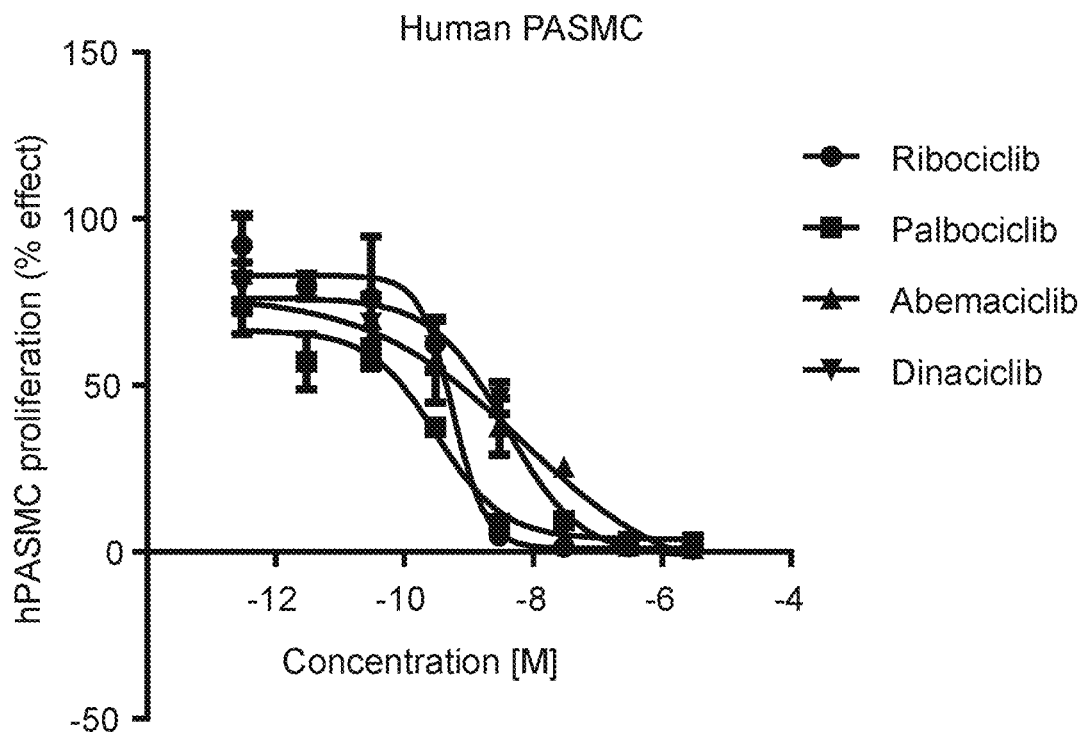

It should be noted that due to experimental logistics, the human PASMC donor cells associated with FIGS. 1a and 1b, and FIGS. 2a and 2b were generated using cells from one donor, and data associated with FIG. 1e and FIG. 2c were generated from a different donor. Likewise, the human PAAF supporting FIGS. 1c and 1f were derived from different donor cells. Finally, the rat PASMC preparations for FIGS. 1d and 1g were generated from cell preparations derived from different animals. There were also differences between assays as discussed in Example 1.

TABLE 1

Inhibition of Proliferation in hPASMC, hPAAF and rPASMC

Figure 1F:
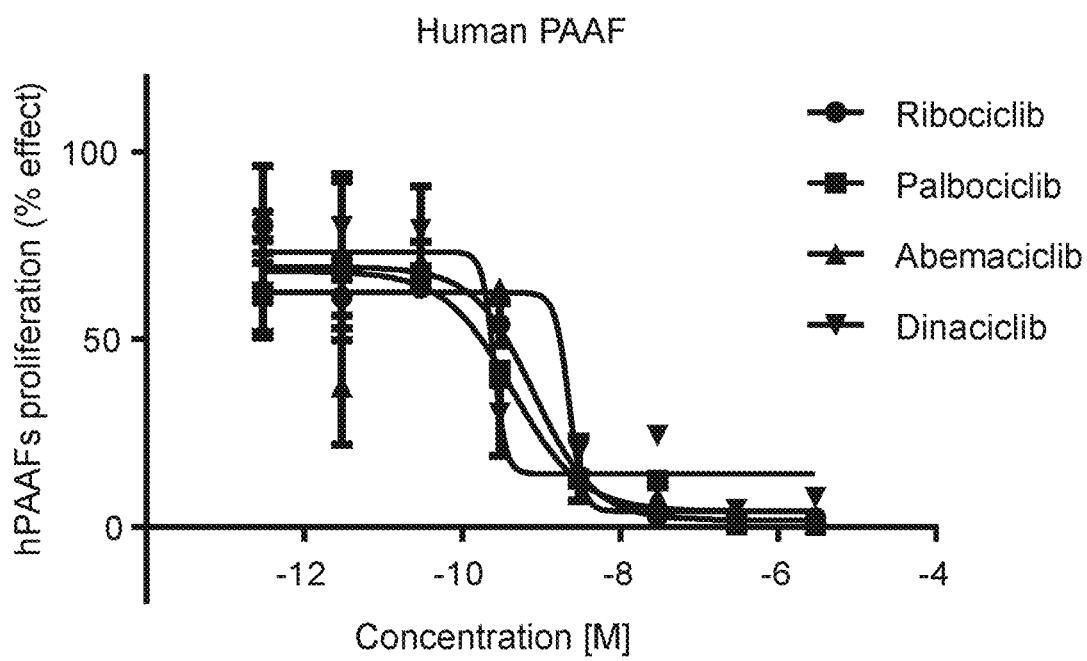

| Compound | hPASMC $IC_{50}$ (nM) N = 6 FIG. 1e | hPAAF $IC_{50}$ (nM) N = 6 FIG. 1f | rPASMC $IC_{50}$ (nM) N = 6 FIG. 1g |
|---|---|---|---|
| Palbociclib | 0.3 | 0.4 | 19 |
| Abemaciclib | 6.5 | 1.2 | 13 |
| Dinaciclib | 4.0 | 0.2 | 1.1 |
| Ribociclib | 0.5 | 0.8 | 28.6 |

Palbociclib was then examined for its effects on the phosphorylation of Rb in human PASMCs using in-cell western analysis. See Example 1. Palbociclib potently inhibited PDGF-BB or serum-induced Rb phosphorylation with an $IC_{50}$ of 5.2 nM (FIG. 2b) and 14.9 nM (FIG. 2a), respectively. Thus, palbociclib is highly effective in blocking the proliferation of the key cell types involved in pathological vascular remodeling in PAH.

In additional studies, where palbociclib was run in parallel with abemaciclib, dinaciclib and ribociclib, proliferation was induced using 10% FBS, and all CDK inhibitors demonstrated inhibition of the induced Rb phosphorylation. See Table 2 based on data as presented in FIG. 2c, where the percent effect is calculated similarly to the percent effect for proliferation.

TABLE 2

Inhibition of Phosphorylation of Rb in hPASMCs

| Compound | Average $IC_{50}$ (nM), N = 6 |
|---|---|
| Palbociclib | 64.18 |
| Dinaciclib | 5.65 |
| Abemaciclib | 262.04 |
| Ribociclib | 351.83 |

MCT has been shown to induce pulmonary vascular injury primarily after hepatic generation of the toxic metabolite, monocrotaline pyrrole. The MCT model offers the advantage of several key aspects of human PAH, including vascular remodeling, proliferation of smooth muscle cells, endothelial dysfunction, upregulation of inflammatory cytokines, and right ventricle (RV) failure. Stenmark, K. R., et al. Animal models of pulmonary arterial hypertension: the hope for etiological discovery and pharmacological cure. *American journal of physiology. Lung cellular and molecular physiology* 297, L1013-1032 (2009). For the FIGS. 3 and 4, Palbo is palbociclib, Sild is sildenafil, Rio is riociguat, and Veh is vehicle. In the MCT PAH model described in Example 3, rats exposed to MCT consistently developed pulmonary hypertension, with an increase of mean (MPAP), systolic (SPAP), and diastolic (DPAP) pulmonary arterial pressures. The Fulton Index was also increased after MCT exposure. The Fulton Index is the following ratio based on the weight of:

right ventricle [RV]/(left ventricle [LV]+septum [S])

For these studies, an agent was considered to be administered prophylactically when the agent was first administered on day 0, the same day on which a second agent, e.g., MCT, was also administered to cause PAH symptoms to develop in the model. However, an agent was considered to be administered therapeutically when the agent was administered after the animal had developed symptoms of PAH, e.g., the agent was first administered on day 14 of the study.

As expected, sildenafil (50 mg/kg/dose; PO BID), when dosed prophylactically (day 0-28), significantly reduced PAH-related increases in MPAP (FIG. 3b), SPAP (FIG. 3h), DPAP (FIG. 3i), Fulton Index (FIG. 3c) and heart weight (FIG. 3j). When administered therapeutically (day 14-28); however, sildenafil, an approved therapy for PAH, only demonstrated a small and non-significant reduction in MPAP, SPAP, DPAP, Fulton index and heart weight in this study.

Palbociclib (100 mg/kg/day; PO; QD), when administered therapeutically (day 14-28), far exceeded expectations. FIG. 3a shows frequency of administration of drugs studied. Palbociclib not only matched but exceeded the positive hemodynamic and physiologic effects of sildenafil when dosed prophylactically.

Histomorphometrically, palbociclib, but not sildenafil, dramatically improved and in some cases fully normalized structural changes in the pulmonary vasculature (FIG. 3f). The palbociclib-dosed group (day 14-28) had significantly lower (down to 0.58x MCT) average vessel wall thickness (elastin staining) for both intra-acinar (≤50 µm external diameter) and pre-acinar (51-100 µm external diameter) pulmonary arteries compared with vehicle/MCT-dosed group, exceeding the beneficial effects of sildenafil (day 0-28) (0.76x MCT), while the sildenafil group (day 14-28) had little effect on these measurements. (FIG. 3d). Palbociclib (day 14-28) also caused a greater reduction of the density of fully muscularized intra-acinar vessels than sildenafil, which was only effective while dosed from day 0 to 28. (αSMA staining; FIG. 3e). In addition, the palbociclib-dosed group (day 14-28) also had significantly lower disease severity scores (range 0-2; mean 1) compared with vehicle/MCT-dosed group (range 1-4; mean 3), again outperforming the sildenafil-dosed group (day 0-28; range 1-4; mean 2.5) (FIG. 3g).

Chronic hypoxia plus vascular endothelial growth factor (VEGF) receptor blockade (Semaxinib/Su5416) cause severe PAH in rats. Stenmark, K. R., infra. In the Su5416/Hx PAH model, as described in Example 4, palbociclib (100 mg/kg/day; PO; QD) was evaluated against two drugs commonly used to treat PAH patients: sildenafil (30 mg/kg/dose; PO; BID) and riociguat (10 mg/kg/day, PO; QD). Lang, M., et al. The soluble guanylate cyclase stimulator riociguat ameliorates pulmonary hypertension induced by hypoxia and SU5416 in rats. *PloS one* 7, e43433 (2012). All three drugs were administered from days 7 to 28 (FIG. 4a). Although prophylactic treatment with sildenafil significantly reduced MPAP (FIG. 4b), SPAP (FIG. 4h) and DPAP (FIG. 4i), and prophylactic treatment with riociguat significantly reduced MPAP and DPAP as expected, therapeutic treatment using either agent resulted in only a slight reduction in Fulton Index in this study, and no change in lung or heart weights when compared with the vehicle/Su5416/Hx group. Palbociclib, however, restored hemodynamic endpoints closer to the non-diseased control group, superseding both sildenafil and riociguat (FIG. 4b comparing MPAP results and FIG. 4c comparing Fulton Index values). When looking at therapeutic treatments, only the palbociclib group showed a significant reduction in Fulton index (FIG. 4c) and heart weight (FIG. 4j).

Histomorphometrically, palbociclib, but not sildenafil or riociguat, dramatically improved and in some cases fully normalized structural changes in the pulmonary vasculature (FIG. 4f). Histomorphometric analysis showed that palbociclib, but not riociguat or sildenafil, significantly reduced average vessel wall thickness for both intra-acinar and pre-acinar vessels (FIG. 4d). The palbociclib-dosed group also had significantly lower (0.68x Su5416/Hx) muscularized intra-acinar vessel density compared with vehicle/Su5416/Hx group. Sildenafil- and Riociguat-dosed group means were not statistically significantly different from vehicle/SuHx group (FIG. 4e). In addition, the palbociclib-dosed group had almost fully normalized disease severity scores (range 0-1.5; mean 0.25) compared with vehicle/Su5416/Hx group (range 3-4; mean 3.65), outperforming the sildenafil- and riociguat-dosed groups (FIG. 4g). Surprisingly, palbociclib treatment resulted in near-complete suppression of hemodynamic changes and significant structural improvement in the pulmonary vasculature in the rat Su5416/Hx PAH model, outperforming both sildenafil and riociguat.

IHC analysis of dual αSMA/Ki67- and dual CD31/phosphoRb-stained rat lung sections (FIG. 5a and FIG. 5b) from the in vivo studies showed that MCT caused a significant increase of vessel-associated Ki67$^+$ proliferating cells (FIG. 5c) and a trend of increase in numbers of vessel-associated phoshoRb$^+$ cells (FIG. 5d). See Example 5. These target-specific endpoints were dramatically decreased to control levels by palbociclib administration (FIG. 5c). Similarly, Su5416/treatment combined with hypoxia induced significant increases in vessel-associated Ki67$^+$ and pRb$^+$ cells in the pulmonary vasculature. Palbociclib fully reversed these increases; whereas, sildenafil or riociguat showed no significant beneficial effect on these biomarkers. Palbociclib suppressed cell proliferation in the pulmonary vasculature in PAH disease models.

The invention includes a method of treating PAH, or a disorder disclosed herein, where the method includes using palbociclib as monotherapy or also in a combination therapy in which a patient in need of treatment is administered palbociclib in combination with one or more drugs (referred to also as active agent) approved for the treatment of PAH, for the treatment of a PAH associated condition, or for the treatment of a disorder disclosed herein, or as combination thereof. For example, an additional active agent may include but is not limited to a prostaglandin (e.g., epoprostenol, treprostinil, iloprost, selexipag), an endothelin receptor antagonist (e.g., bosentan, ambrisentan, macitentan), a guanylate cyclase inhibitor (e.g., riociguat), vasodilators (e.g., prostacyclin and sildenafil), calcium channel blockers (e.g., amlodipine, diltiazem, and nifedipine); anticoagulants (e.g., warfarin), and diuretics. Reference to a drug, e.g., sildenafil, includes sildenafil and all pharmaceutically acceptable salts, e.g., sildenafil citrate.

In another aspect, palbociclib is used in the manufacture of a medicament for the treatment or prevention of PAH. Yet in another aspect, palbociclib is used in the manufacture of a medicament for the treatment or prevention or related diseases as discussed herein. In various embodiments, the medicament is formulated for oral administration, including both immediate release and sustained release pharmaceutical formulations. In other embodiments the medicament is formulated for administration by inhalation. In all of these embodiments, the invention provides unit dose forms of the medicament The present invention also includes isotopically labelled compounds, which are identical to palbociclib, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2$H, $^3$H, $^{13}$C, $^{11}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^3$H and $^{14}$C are incorporated, are useful in drug and/or substrate tissue distribution assays. Tritiated, i.e., $^3$H, and carbon-14 i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled palbociclib and prodrugs thereof can generally be prepared by carrying out the procedures disclosed in the Schemes and/or in the Examples and Preparations below, by substituting a readily available isotopically labelled reagent for a non-isotopically labelled reagent.

When referring to palbociclib herein, it includes 6-acetyl-8-cyclopentyl-5-methyl-2-{[5-(piperazin-1-yl)pyridin-2yl]amino}pyrido[2,3-d]pyrimidin-7(8H)-one, or pharmaceutically acceptable salts thereof forming pharmaceutically acceptable formulations comprising salts, including but not limited to acid addition salts, solvates and N-oxides of palbociclib. See WO 03/062236, incorporated herein by reference.

The term "subject", as used herein, refers to a human, primate, companion animals (including cat or dog). The term "subject" includes a patient.

The term "treating", as used herein, refers to reversing, alleviating, inhibiting the progress of, or preventing the disorder or condition to which such term applies, or preventing one or more symptoms of such condition or disorder. The term "treatment", as used herein, refers to the act of treating, as "treating" is defined immediately above.

Palbociclib can be formulated and administered in a wide variety of oral and parenteral dosage forms, including transdermal and rectal administration. It will be recognized to those skilled in the art that the following dosage forms may comprise as the active component, palbociclib or a corresponding pharmaceutically acceptable salt or solvate of palbociclib.

This invention also comprises a pharmaceutical formulation comprising a therapeutically effective amount of palbociclib together with a pharmaceutically acceptable carrier, diluent, or excipient therefor. For preparing pharmaceutical compositions with the compounds of the present invention, pharmaceutically acceptable carriers can be either a solid or liquid. Solid form preparations include powders, tablets, pills, capsules, cachets, suppositories, and dispensable granules. A solid carrier can be one or more substances which may also act as diluents, flavoring agents, binders, preservatives, tablet disintegrating agents, or an encapsulating material. For tablet dosage forms, depending on dose, palbociclib may make up from 1 wt % to 80 wt % of the dosage form, typically from 5 wt % to 60 wt %, more typically from about 10 wt % to about 35 wt %, or even more typically from about 15 wt % to about 25 wt % of the dosage form. In specific embodiments, palbociclib comprises about 20 wt % of the dosage form by weight.

In the solid dosage forms of the invention, the carrier may comprise a variety of pharmaceutically acceptable excipients, including, for example, diluents, disintegrants, binders, lubricants, glidants and surface-active agents. Formulations may also include excipients such as preservatives, antioxidants, flavors and colorants, as well as other excipients known in the art.

Solid dosage forms, such as tablets, typically contain diluents, e.g., lactose (monohydrate, spray-dried monohydrate, anhydrous and the like), mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers, polyethylene oxide, hydroxypropyl methyl cellulose and mixtures thereof. Different types of microcrystalline cellulose may be suitable for use in the formulations described herein. Examples of microcrystalline cellulose include Avicel® types: PH101, PH102, PH103, PH105, PH 112, PH113, PH200, PH301, and other types of microcrystalline cellulose, such as silicified microcrystalline cellulose (SMCC). In some embodiments, the diluent is selected from the group consisting of microcrystalline cellulose, lactose monohydrate, mannitol, sorbitol, xylitol, magnesium carbonate, dibasic calcium phosphate, tribasic calcium phosphate, or mixtures thereof. In certain embodiments, the diluent comprises microcrystalline cellulose. In some embodiments, the diluent comprises one or more types of microcrystalline cellulose, for example Avicel® PH105, Avicel® PH200 or mixtures thereof. In some such embodiments, the diluent excludes lactose monohydrate. In other such embodiments, the diluent comprises microcrystalline cellulose and further comprises lactose monohydrate. Diluents frequently comprise from about 25 wt % to about 75 wt % of the solid dosage form, and preferably from about 50 wt % to about 75 wt % of the dosage form.

Solid dosage forms frequently contain disintegrants. Examples of disintegrants include sodium starch glycolate, sodium carboxymethyl cellulose, calcium carboxymethyl cellulose, croscarmellose sodium, crospovidone, polyvinylpyrrolidone, methylcellulose, microcrystalline cellulose, lower alkyl-substituted hydroxypropyl cellulose, starch, pregelatinized starch, and sodium alginate. In some embodiments, the disintegrant is crospovidone. Any grade of crospovidone can be used; for example CL, CL-SF and XL grades of crospovidone are suitable for use in the formulations described herein. Specific examples include Kollidon, Kollidon CL®, Kollidon CL-M®, Polyplasdone XL®, Polyplasdone XL-10®, and Polyplasdone INF-10®. In some embodiments, the carrier comprises at least one disintegrant selected from the group consisting of crospovidone, croscarmellose sodium and sodium starch glycolate. In specific embodiments, the disintegrant is crospovidone. Disintegrants frequently comprise from about 1 wt % to about 25 wt %, preferably from about 5 wt % to about 20 wt %, more preferably from about 5 wt % to about 10 wt % of the dosage form.

Binders may be used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose, and hydroxypropyl methylcellulose. In some embodiments, the binder is selected from the group consisting of microcrystalline cellulose, hydroxypropyl cellulose and hydroxypropyl methylcellulose. In specific embodiments, the binder is microcrystalline cellulose, e.g. Avicel® PH105. When present, binders may comprise from about 0 wt % to about 15 wt %, or from about 0.2 wt % to about 10 wt % of the dosage form. In some embodiments, the binder comprises about 5 wt % to about 10 wt % of the dosage form. In particular embodiments, the binder comprises about 10 wt % of the dosage form.

Solid dosage forms frequently contain one or more lubricants. Examples of lubricants include magnesium stearate, calcium stearate, zinc stearate, sodium stearyl fumarate, mixtures of magnesium stearate with sodium lauryl sulfate, or mixtures of two or more of these. In some embodiments, the lubricant is magnesium stearate and/or sodium stearyl fumarate. In some embodiments, the lubricant is magnesium stearate. In some such embodiments, the solid dosage form is a tablet comprising intragranular and extragranular magnesium stearate. In other embodiments, the solid dosage form is a tablet comprising intragranular magnesium stearate and extragranular sodium stearyl fumarate. When present, lubricants frequently comprise from about 0.25 wt % to about 10 wt %, preferably from about 0.5 wt % to about 6 wt % of the dosage form.

Tablets may also compromise glidants, for example silicon dioxide, colloidal silicon dioxide, magnesium silicate, magnesium trisilicate, talc, and other forms of silicon dioxide, such as aggregated silicates and hydrated silica. In some embodiments, the glidant is silicon dioxide. When present, glidants may comprise from about 0 wt % to about 10 wt %, preferably from about 0.2 wt % to about 5 wt %, or from about 0.5 wt % to about 2 wt % of the tablet.

Tablets may optionally include surface-active agents, such as sodium lauryl sulfate and polysorbate 80. When present, surface-active agents may comprise from 0 wt % to 10 wt %, or preferably 0.2 wt % to 5 wt % of the tablet.

In general, the solid dosage forms of the invention are prepared according to methods usual in pharmaceutical chemistry. Selected excipients may be incorporated along with the active pharmaceutical ingredient into either or both of the extragranular or intragranular compartments.

The therapeutically effective dose of palbociclib will vary from approximately 0.01 mg/kg to approximately 100 mg/kg of body weight per day. Typical adult doses will be approximately 0.1 mg to approximately 3000 mg per day. More typically, the therapeutically effective adult dose of palbociclib is 75 mg, 100 mg or 125 mg per day. The quantity of active component in a unit dose preparation may be varied or adjusted from approximately 0.1 mg to approximately 500 mg, preferably about 25 mg to about 125 mg according to the particular application. The composition can, if desired, also contain other compatible therapeutic agents. A subject in need of treatment with palbociclib is administered a dosage of about 0.6 to about 500 mg per day, and preferably about 25 mg to 125 mg per day, either singly or in multiple doses over a 24-hour period. Such treatment may be repeated at successive intervals for as long as necessary.

ASSAY EXAMPLES

Example 1

Cell proliferation assay. Primary PASMCs and PAAFs from normal human subjects (ScienCell Research Laboratories, San Diego, Calif., USA) and rat primary PASMCs (Cell Applications, San Diego, Calif., USA) were plated in CellBIND® 96-well plates in Dulbecco's modification of Eagle's medium (DMEM) containing 5% fetal bovine serum (FBS), and serum-starved for 24 h in DMEM containing 0.1% FBS. Cells were first pre-incubated with different concentrations of palbociclib (in triplicates) for 30 minutes, and then 30 ng/ml PDGF-BB or 5% FBS was added to stimulate cell proliferation. Cells were maintained for 48 h before the proliferation rate was evaluated using the Cell Proliferation ELISA BrdU (bromodeoxyuridine) Luminescence Kit (Roche Diagnostics, Mannheim, Germany). BrdU was added to the medium 16 h before the quantification of BrdU incorporation. This procedure was use to generate data as presented in at least FIGS. 1a, 1b, 1c, and 1d. $IC_{50}$ values were calculated for any given inhibitor by determining the concentration of compound needed to inhibit 50% of the response applied to the system. $IC_{50}$ values were derived from the four parameter logistic equation which was fit to the compound concentration response data.

Alternatively, rather than using BrdU, EdU (5-ethynyl-2'-deoxyuridine) can be used. Cells were first pre-incubated with different concentrations of the CDK inhibitor for 30 minutes, and then 5% FBS was added to stimulate cell proliferation. Cells were maintained for 24 h before the proliferation rate was evaluated using EDU Click-iT EdU Alexa Fluor® 647 HCS Assay (Thermofisher Scientific, USA). EdU was added to the medium 16 h before the quantification of EdU incorporation. Proliferation was quantified by scanning the 96-well plates using automated high content imaging platform equipped with appropriate fluorescence microscopic filters for DAPI (4',6-Diamidino-2-Phenylindole) or Hoechst stain and Cyanine5 dyes as part of the Click-iT assay. Proliferating EdU positive cells detected at Cyanine5 were quantified and normalized to total cell number per well where the total cell number per cell was identified by DAPI or Hoechst signal. The % effect was then calculated:

$$\frac{\left(\begin{array}{c}\text{Avg amt of proliferating cells per concentration}-\\ \text{Avg min } \textit{amt of prolif'n}\end{array}\right)}{\left(\begin{array}{c}\text{Avg max } \textit{amt of prolif'n} -\\ \text{Avg minimum} \textit{amt of prolif'n}\end{array}\right)}$$

The average (avg) amount (amt) of proliferating cells per concentration of CDK inhibitor with FBS present. The CDK inhibitors used were palbociclib, abemaciclib, dinaciclib, and ribociclib.

The minimum amount of proliferation (min amt of prolif'n) is based on cell numbers in the wells where FBS is not added and no CDK inhibitor is present.

The maximum amount of proliferation (max amt of prolif'n) is based on cell numbers in the wells where FBS is added and no CDK inhibitor is present.

This procedure was used to generate data as presented in at least FIGS. 1e, 1f, and 1g.

In-cell western analysis. Primary PASMCs from normal human subjects were cultured and serum-starved as described above. Cells were first pre-incubated with different concentrations of palbociclib for 60 minutes, and then either 5% FBS or 10% FBS or 30 ng/ml PDGF-BB was added to stimulate cell proliferation and Rb phosphorylation. The effect of Palbociclib on Rb phosphorylation was evaluated 24 h later, using in-cell western assay according to the manufacturer's instructions (Li-Cor Biosciences, Lincoln, Nebr., USA). Phosphorylated Rb was measured using a rabbit monoclonal antibody anti-phospho-Rb (Ser807/811) (Cell Signaling Technology, Inc., Danvers, Mass., USA), followed by detection with IRDye 800CW infrared fluorescent dye-labeled goat anti-rabbit secondary antibody. Actin levels were measured using mouse anti-actin monoclonal antibodies (pan Ab-5) (Fisher Scientific Pittsburgh, Pa., USA; Sigma Aldrich, St. Louis, Mo., USA), and followed by detection with IRDye 680RD-labeled goat anti-mouse secondary antibody. See FIG. 2a where 5% FBS was used, FIG. 2b where PDGF-BB was used, and FIG. 2c where 10% FBS was used.

Example 2

Rat MCT-induced PAH Model: Male Sprague-Dawley rats (Charles River Laboratories) (260-280 g; vehicle control group, n=6; all other groups, n=15) received MCT (50 mg/kg, SC; 1 ml/kg BVV) dissolved in vehicle (33.3% 1 N HCl, 14.8% 1 N NaOH, 52.2% di$H_2$O) or vehicle alone on day 0. Sildenafil (50 mg/kg/dose; BID) was administered (5 ml/kg, PO) either prophylactically from days 0-28 or therapeutically from days 14-28. Palbociclib (100 mg/kg; QD) was administered therapeutically (days 14-28). Both sildenafil and palbociclib were resuspended in vehicle (0.5% methylcellulose) and administered orally (5 ml/kg). On day 28, animals were anesthetized via isoflurane, hemodynamic parameters were evaluated, and tissues harvested after euthanasia.

Example 3

Rat MCT-induced PAH Model: Male Sprague-Dawley rats (Charles River Laboratories) (260-280 g; vehicle control group, n=6; all other groups, n=15) received MCT (50 mg/kg, SC; 1 ml/kg BVV) dissolved in vehicle (33.3% 1 N HCl, 14.8% 1 N NaOH, 52.2% di$H_2$O) or vehicle alone on day 0. Sildenafil (50 mg/kg/dose; BID) was administered (5 ml/kg, PO) either prophylactically from days 0-28 or therapeutically from days 14-28. Palbociclib (100 mg/kg; QD) was administered therapeutically (days 14-28). Both sildenafil and palbociclib were resuspended in vehicle (0.5% methylcellulose) and administered orally (5 ml/kg). On day 28, animals were anesthetized via isoflurane, hemodynamic parameters were evaluated, and tissues harvested after euthanasia.

Hemodynamic measurements—monocrotaline (MCT) study: On day 28, animals were anesthetized via 2% isofluorane in positive pressure ventilator. Pulmonary hemodynamics were measured using a pre-calibrated pressure transducer in isoflurane positive-pressure ventilated animals. Steady-state pulmonary and systemic arterial pressures were measured using a Millar Solid State Mikro-tip catheter (Millar Instruments, Houston, Tex.) introduced to the pulmonary arterial trunk at the level of the aortic arch via the right carodid artery. Hemodynamic values were automatically calculated by the physiological data acquisition system, ADI Chart (ADI Instruments, Colorado Springs, Colo.) (Plato BioPharma).

Example 4

SuHx-induced Pulmonary Arterial Hypertension: Sprague-Dawley rats were obtained from Charles River Laboratories (200-300 g; vehicle control, n=5; all other groups, n=10). Rats received Semaxinib dissolved in DMSO on day 0, followed by housing in low (13%) oxygen until day 28. Sildenafil (30 mg/kg/dose; BID), Riociguat (10 mg/kg, QD) or Palbociclib (100 mg/kg; QD) was administered in vehicle (0.5% methylcellulose) from days 7-28. Terminal hemodynamic evaluations and necropsy were conducted on day 28 in a manner similar to the MCT study.

Hemodynamic measurements Su/Hx study: On day 28, animals were anesthetized via intramuscular injection of ketamine/xylazine (80/10 mg/kg). A Millar catheter was inserted into the pulmonary artery and pulmonary pressure and hemodynamics were measured as described by Stringer et al., (1981) Catheterization of the pulmonary artery in the closed-chest rat. *J. Appl. Physiol.* 51, 1047-1050. Hemodynamic values were calculated using the NOTOCORD-Hem software (NOTOCORD, Inc., Croissy sur Sienne, France) (CorDynamics).

Measurement of RV hypertrophy. After collection of the heart at necropsy, the atria and great vessels were removed. The RV was separated from the LV and S. The wet weights of the RV and LV+S were measured to calculate the Fulton Index.

Example 5

Tissue preparation. Under anesthesia, the animals were exsanguinated, and the pulmonary circulation flushed with oxygenated (animals from Example 3 [MCT]) or heparizined (animals from Example 4 [Su5416/Hx]) saline. Trachea, lungs, and heart were removed intact from thoracic cavity and placed in ice-cold saline. Right lung lobes were removed, weighed, and immediately flash frozen in liquid nitrogen. A 10 mL syringe filled with fixative (10% NBF) with attached blunt tip needle (20 g) was used to inflate the left lung lobe and the airway was tied off to keep it consistently expanded. The left lung was then immersion fixed in 10% NBF for 48 hrs and then transferred to 70% EtOH for ≤5 days.

Histomorphometric analysis. Three, 3-5 µm thick, transverse sections of the left lung lobe were used for histomorphometric analysis. Overall disease severity scores were determined by light microscopic evaluation of hematoxylin and eosin (H&E)-stained lung sections by a board-certified veterinary pathologist. Scores ranged from 0 (absent), 1 (minimal), 2 (mild), 3 (moderate), 4 (marked) to 5 (severe) and were assigned according to the approximate percentage of the tissue affected by the tissue changes (inflammatory, degenerative, vascular and/or proliferative) characteristic of the PAH model. Average vessel wall thickness was evaluated using lung sections prepared with a modified Verhoeff-van Gieson elastin stain. Image analysis was performed using random field sampling (Visiopharm newCAST) of 10% of tissue area with observer-assisted identification of intra-acinar and pre-acinar vessels and application of a nucleator probe to measure vessel wall thickness. Fully muscularized intra-acinar vessel density was evaluated in a similar manner using dual αSMA/Ki67 IHC-stained sections and observer-assisted counting of ≥70% muscularized (i.e. SMA$^+$), transversely sectioned, ≤50 µm external diameter, intra-acinar vessels with an identifiable lumen. Vessel-associated Ki67$^+$ and pRb$^+$ cells were counted in αSMA/Ki67 IHC-and CD31/pRb IHC-stained lung sections, respectively, using random field sampling of 10% of tissue area and observer-assisted identification of Ki67$^+$ or pRb$^+$ cells associated with the walls (i.e. in the intima or media) of vessels 100 µm external diameter.

Immunohistochemistry. Dual α-SMA/Ki67 nuclear antigen: All IHC steps were performed on 3 µm-thick, formalin-fixed, paraffin-embedded (FFPE) sections on Leica Bond Rx automated immunohistochemistry stainer. The instrument was programmed to bake and dewax the slides. The primary antibody, anti-human αSMA (rabbit polyclonal ab5694, Abcam, Cambridge, Mass.) was diluted 1:200 in Bond™ Primary Antibody Diluent (PV6123), applied to the slides, incubated for 30 minutes and detected using Bond™ Polymer Refine AP-Red detection kit (DS9390, Leica Biosystems, Buffalo Grove, Ill.). This step was followed by a 20-minute, heat-induced epitope retrieval using Bond™ Epitope Retrieval 1 (ER1) solution (AR9961, Leica Biosystems). The secondary antibody, anti-Ki67 (mouse monoclonal Ki-67 [MM1] nuclear antigen RTU, PA0118 [Leica]) was applied for 15 minutes followed by detection with Bond™ Polymer Refine HRP DAB detection system (DS9800). Slides were counterstained, dehydrated and coverslipped.

Dual CD31/phosphoRb: The initial steps were the same as above. Heat-induced epitope retrieval was performed for 20 minutes with Bond™ Epitope Retrieval 2 (ER2) solution (AR9640). The primary antibody, anti-phosphoRb (rabbit polyclonal phospho-Rb [ser807/811], 9308, Cell Signaling Technology, Danvers, Mass.) diluted 1:600 in Bond™ Primary Antibody Diluent was applied to the slides and incubated for 30 minutes. Bond™ Polymer HRP-DAB Refine detection kit was used subsequent to primary antibody. This step was followed by a 10-minute, heat-induced epitope retrieval using Bond™ Epitope Retrieval 1 (ER1) solution (AR9961, Leica Biosystems). The secondary antibody, anti-CD31 (rabbit monoclonal [EPR3094], ab76533, Abcam, Cambridge, Mass.) was applied for 45 minutes followed by detection with Bond™ Polymer Refine AP-Red detection kit (DS9390, Leica Biosystems). Slides were counterstained, dehydrated and cover-slipped.

Statistical Analysis

Data are presented as the mean±S.E.M. Statistical analyses between groups were performed using one-way analysis of variance (ANOVA) followed by Tukey multiple comparison test (GraphPad Prism 6, GraphPad Software, San Diego, Calif., USA). The level of statistical significance was set at the multiplicity adjusted P value of 0.05 (labelled as † or *), or 0.01 (labelled as †† or **).

What is claimed is:
1. A method for treating pulmonary artery hypertension (PAH) in a human in need thereof, which method comprises administering to the human an effective amount of an inhibitor of CDK4 and CDK6 selected from the group consisting of:
6-acetyl-8-cyclopentyl-5-methyl-2-{[5-(piperazin-1-yl) pyridin-2yl]amino}pyrido[2,3-d[pyrimidin-7(8H)-one,
7-cyclopentyl-N, N-dimethyl-2-((5-(piperazin-1-yl)pyridin-2-yl)amino)-7H-pyrrolo[2,3-d]pyrimidine-6-carboxamide, or

2-pyrimidinamine, N-(5-((4-ethyl-1-piperazinyl)methyl)-
2-pyridinyl)-5-fluoro-4-(4-fluoro-2-methyl-1-(1-
methylethyl)-1H-benzimidazol-6-yl),
or pharmaceutically acceptable salts thereof.

2. The method of claim 1, wherein the inhibitor of CDK4 and CDK6 is 7-cyclopentyl-N,N-dimethyl-2-((5-(piperazin-1-yl)pyridin-2-yl)amino)-7H-pyrrolo[2,3-d]pyrimidine-6-carboxamide, or pharmaceutically acceptable salts thereof.

3. The method of claim 1, wherein the inhibitor of CDK4 and CDK6 is 2-pyrimidinamine, N-(5-((4-ethyl-1-piperazinyl)methyl)-2-pyridinyl)-5-fluoro-4-(4-fluoro-2-methyl-1-(1-methylethyl)-1H-benzimidazol-6-yl), or pharmaceutically acceptable salts thereof.

* * * * *